(12) United States Patent
Hobbs et al.

(10) Patent No.: US 11,918,745 B2
(45) Date of Patent: Mar. 5, 2024

(54) NEONATAL FLEXIBLE AND HYBRID MEDICAL TUBES

(71) Applicant: Fisher & Paykel Healthcare Limited, Auckland (NZ)

(72) Inventors: Gareth James Hobbs, Auckland (NZ); Layton Robert Hern, Auckland (NZ); Kiel Anthony McCool, Auckland (NZ); Elmo Benson Stoks, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 436 days.

(21) Appl. No.: 16/616,929

(22) PCT Filed: May 25, 2018

(86) PCT No.: PCT/NZ2018/050074
§ 371 (c)(1),
(2) Date: Nov. 25, 2019

(87) PCT Pub. No.: WO2018/217105
PCT Pub. Date: Nov. 29, 2018

(65) Prior Publication Data
US 2020/0147336 A1 May 14, 2020

Related U.S. Application Data

(60) Provisional application No. 62/511,788, filed on May 26, 2017.

(51) Int. Cl.
*A61M 16/08* (2006.01)
*A61G 11/00* (2006.01)
(Continued)

(52) U.S. Cl.
CPC ......... *A61M 16/0875* (2013.01); *A61G 11/00* (2013.01); *A61M 16/0816* (2013.01);
(Continued)

(58) Field of Classification Search
CPC .............. A61M 16/0066; A61M 16/08; A61M 16/0816; A61M 16/0833; A61M 16/0875;
(Continued)

(56) References Cited

U.S. PATENT DOCUMENTS

| | | | |
|---|---|---|---|
| 3,307,589 | A | 3/1967 | Sheffield |
| 3,349,806 | A | 10/1967 | Roberts |

(Continued)

FOREIGN PATENT DOCUMENTS

| | | | | |
|---|---|---|---|---|
| CA | 2976393 | | 9/2016 | |
| DE | 10021111 | A1 * | 11/2001 | ............ A61M 16/08 |

(Continued)

OTHER PUBLICATIONS

Machine translation of DE-10021111-A1.*
International Search Report; PCT/NZ2018/050074; dated Sep. 17, 2018; 16 pages.

*Primary Examiner* — Joseph D. Boecker
(74) *Attorney, Agent, or Firm* — Knobbe Martens Olson & Bear LLP

(57) ABSTRACT

Medical tubes and methods of manufacturing medical tubes are disclosed, such as in positive airway pressure (PAP), respirator, anaesthesia, ventilator, and insufflation systems. The tube may be a composite structure made of two or more distinct components spirally wound to form an elongate tube. One of the components may be a spirally wound elongate hollow body, and the other component an elongate structural component spirally wound between turns of the spirally wound hollow body. Alternatively, the tube need not be made from distinct components. For instance, an elongate hollow body formed (e.g., extruded) from a single material may be spirally wound to form an elongate tube. The elongate hollow body itself may in transverse cross-section have a thin wall portion and a relatively thicker or more rigid (Continued)

reinforcement portion. The tubes can be incorporated into a variety of medical circuits or have other medical uses.

20 Claims, 22 Drawing Sheets

(51) Int. Cl.
*A61M 16/00* (2006.01)
*A61M 16/10* (2006.01)
*A61M 16/16* (2006.01)

(52) U.S. Cl.
CPC ...... *A61M 16/109* (2014.02); *A61M 16/1095* (2014.02); *A61M 16/16* (2013.01); *A61M 2016/003* (2013.01); *A61M 16/0066* (2013.01); *A61M 16/161* (2014.02); *A61M 2205/3368* (2013.01); *A61M 2205/3633* (2013.01); *A61M 2240/00* (2013.01)

(58) Field of Classification Search
CPC .... A61M 16/1095; A61M 16/16; A61G 11/00
See application file for complete search history.

(56) References Cited

U.S. PATENT DOCUMENTS

| | | | |
|---|---|---|---|
| 3,891,556 A | 6/1975 | Richardson et al. | |
| 4,808,201 A | 2/1989 | Kertzman | |
| 6,078,730 A * | 6/2000 | Huddart | A61M 16/08 219/536 |
| 6,769,431 B2 * | 8/2004 | Smith | A61M 16/1045 128/203.16 |
| 7,469,719 B2 * | 12/2008 | Gray | F16L 11/115 138/33 |
| 8,037,882 B2 * | 10/2011 | Smith | A61M 16/0891 128/203.16 |
| 8,905,082 B2 * | 12/2014 | Gray | B29C 53/60 138/109 |
| 9,468,733 B2 * | 10/2016 | Graham | B29C 65/4845 |
| 9,533,117 B2 * | 1/2017 | Gray | A61M 16/0875 |
| 9,872,967 B2 * | 1/2018 | Sims | A61M 16/1095 |
| 10,010,693 B2 * | 7/2018 | Sims | A61M 16/1095 |
| 10,080,866 B2 | 9/2018 | Stoks et al. | |
| 10,449,318 B2 | 10/2019 | Graham et al. | |
| 10,478,583 B2 * | 11/2019 | Gray | B29C 53/607 |
| 10,589,050 B2 | 3/2020 | Buswell et al. | |
| 10,688,270 B2 * | 6/2020 | Sims | F16L 53/38 |
| 10,722,663 B2 | 7/2020 | Boyes et al. | |
| 10,751,498 B2 | 8/2020 | Munkelt et al. | |
| 10,828,455 B2 * | 11/2020 | Graham | A61M 16/16 |
| 11,052,215 B2 * | 7/2021 | Sims | F16L 53/38 |
| 11,129,954 B2 | 9/2021 | Buswell et al. | |
| 11,219,733 B2 * | 1/2022 | Gray | B29C 53/36 |
| 11,318,270 B2 | 5/2022 | Stoks et al. | |
| 11,358,318 B2 | 6/2022 | Graham et al. | |
| 2001/0054422 A1 * | 12/2001 | Smith | A61M 16/1065 128/200.24 |
| 2004/0065335 A1 * | 4/2004 | Huber | A61M 16/1075 128/206.21 |
| 2004/0079371 A1 | 4/2004 | Gray | |
| 2005/0165366 A1 | 7/2005 | Brustad et al. | |
| 2008/0047560 A1 * | 2/2008 | Veliss | A61M 16/08 128/206.24 |
| 2011/0247619 A1 | 10/2011 | Formica et al. | |
| 2012/0125333 A1 * | 5/2012 | Bedford | A61M 16/06 128/203.25 |
| 2012/0325219 A1 * | 12/2012 | Smith | A61M 16/06 128/205.25 |
| 2013/0152931 A1 | 6/2013 | Sims et al. | |
| 2014/0373840 A1 * | 12/2014 | Graham | A61M 16/109 128/203.27 |
| 2015/0027204 A1 | 1/2015 | Stoks et al. | |
| 2015/0306333 A1 | 10/2015 | Amadio et al. | |
| 2019/0388640 A1 * | 12/2019 | Graham | A61M 16/1095 |
| 2020/0147334 A1 * | 5/2020 | Gray | B29C 63/0013 |
| 2020/0289782 A1 * | 9/2020 | Sims | B29C 65/4815 |
| 2020/0306464 A1 | 10/2020 | Boyes et al. | |
| 2020/0338295 A1 | 10/2020 | Munkelt et al. | |
| 2021/0069447 A1 * | 3/2021 | Graham | A61M 16/06 |
| 2021/0386957 A1 * | 12/2021 | Sims | F16L 53/38 |
| 2022/0040437 A1 | 2/2022 | Buswell et al. | |
| 2022/0211966 A1 | 7/2022 | Stoks et al. | |

FOREIGN PATENT DOCUMENTS

| | | | | |
|---|---|---|---|---|
| WO | WO 2001/066176 A1 | 9/2001 | | |
| WO | WO 2003/032805 A2 | 4/2003 | | |
| WO | WO 2006/120683 A2 | 11/2006 | | |
| WO | WO 2014/077706 | 5/2014 | | |
| WO | WO-2014077706 A1 * | 5/2014 | | A61G 11/00 |
| WO | WO 2017/043981 | 3/2017 | | |

* cited by examiner

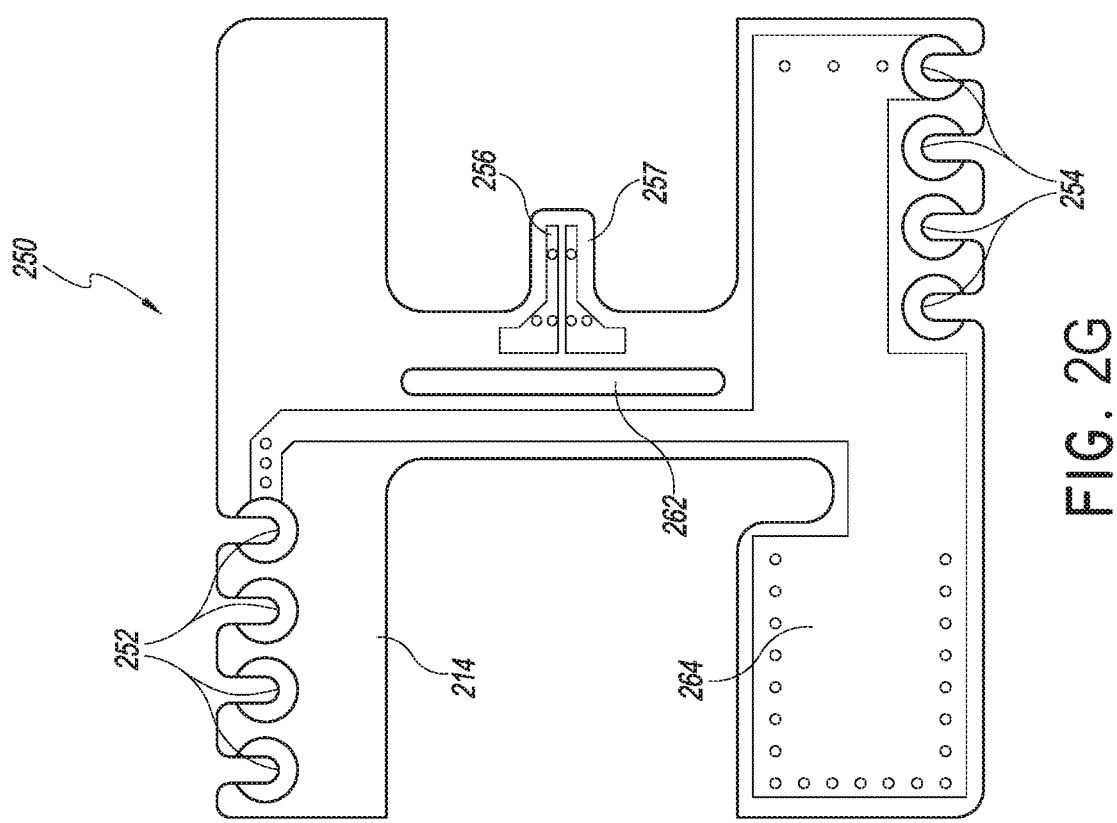
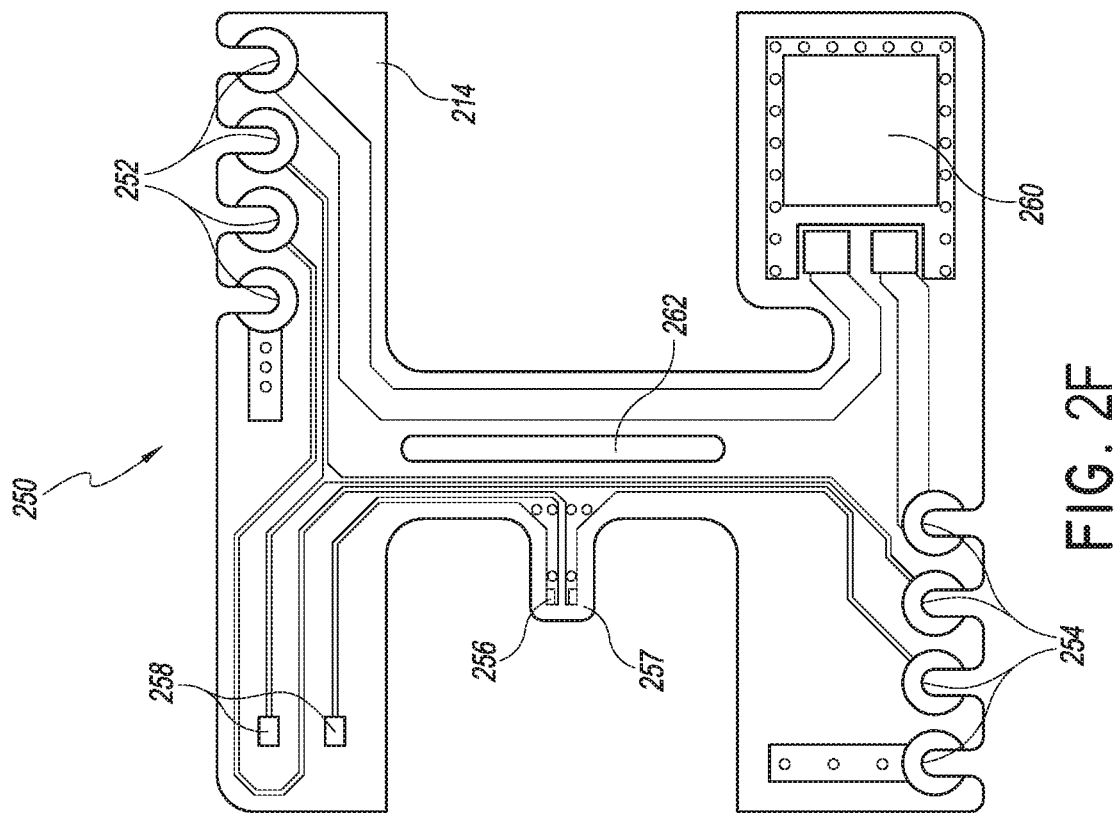

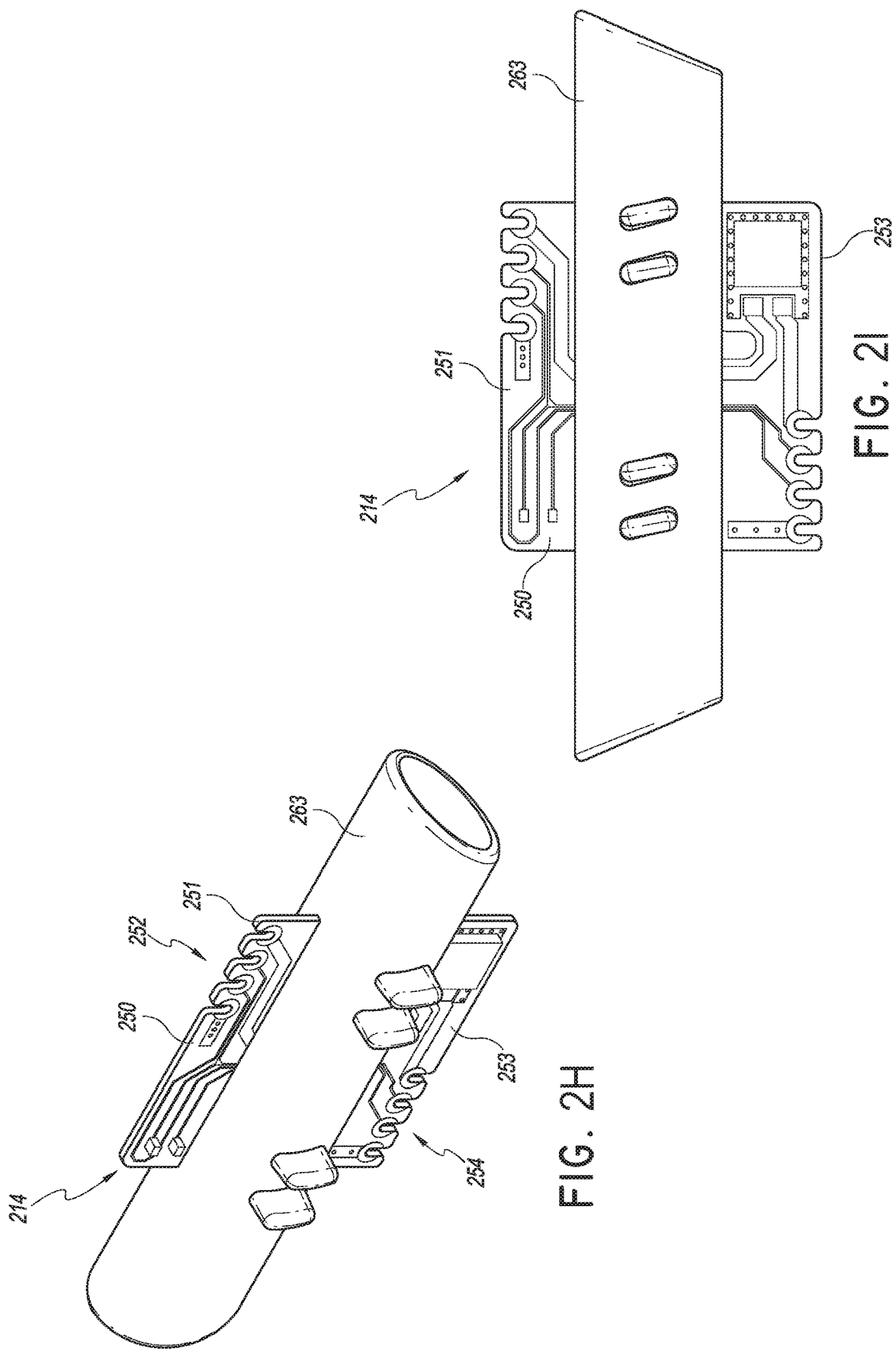

PITCH

NEONATAL FLEXIBLE AND HYBRID MEDICAL TUBES

INCORPORATION BY REFERENCE

The following applications are incorporated by reference herein in their entirety and made part of this specification: U.S. application Ser. No. 14/351,344, entitled "MEDICAL TUBES AND METHODS OF MANUFACTURE," filed Apr. 11, 2014; U.S. application Ser. No. 14/649,801, entitled "MEDICAL TUBES AND METHODS OF MANUFACTURE," filed Jun. 4, 2015; and PCT Application No. PCT/NZ2013/000208, entitled "ZONE HEATING FOR RESPIRATORY CIRCUITS," filed Nov. 14, 2013.

BACKGROUND

Field

This disclosure relates generally to tubes suitable for medical use, and in particular to tubes for use in medical circuits suitable for providing gases to and/or removing gases from a patient.

Description of the Related Art

In medical circuits, various components transport warm and/or humidified gases to and from patients. For example, in some breathing circuits such as PAP or assisted breathing circuits, gases inhaled by a patient are delivered from a heater-humidifier through an inspiratory tube. As another example, tubes can deliver humidified gas (commonly $CO_2$) into the abdominal cavity in insufflation circuits. This can help prevent "drying out" of the patient's internal organs, and can decrease the amount of time needed for recovery from surgery. Unheated tubing allows significant heat loss to ambient cooling. This cooling may result in unwanted condensation or "rainout" along the length of the tubing transporting warm, humidified air. Additionally, users require flexible low weight tubes to improve positionality and usability of tubes when providing respiratory therapy to patients, especially neonatal patients. However, making a low weight flexible tube can cause the tube to experience significant movement and displacement when certain respiratory waveforms are transmitted through the breathing tube.

SUMMARY

Medical tubes and methods of manufacturing medical tubes are disclosed herein in various embodiments, such as in positive airway pressure (PAP), respirator, anaesthesia, ventilator, and insufflation systems. In some embodiments, the tube may be a composite structure made of two or more distinct components that are spirally wound to form an elongate tube. For example, one of the components may be a spirally wound elongate hollow body, and the other component may be an elongate structural component also spirally wound between turns of the spirally wound hollow body In other embodiments, the tube need not be made from distinct components. For instance, an elongate hollow body formed (e.g., extruded) from a single material may be spirally wound to form an elongate tube. The elongate hollow body itself may in transverse cross-section have a thin wall portion and a relatively thicker or more rigid reinforcement portion. The tubes can be incorporated into a variety of medical circuits or may be employed for other medical uses.

Some embodiments provide for a breathing tube. The breathing tube can include a first segment and a second segment. The first segment can have a first flexibility and the second segment can have a second flexibility. The second flexibility can be different than the first flexibility. In certain embodiments, the breathing tube can include an intermediate connector that connects the first segment to the second segment. In certain embodiments, breathing tube can include a substantially inflexible segment that connects the first segment to the second segment.

In some embodiments, the breathing tube can include a sheath around at least one of the first segment or the second segment. The sheath may extend at least a partial length of the at least one segment. In certain embodiments the sheath may extend substantially along the whole length of at least one segment. The sheath can be configured to maintain flexibility and dampen displacement during gas flow through the breathing tube. In some embodiments, the sheath can be a mesh sheath, a braided sheath, or a walled sheath. The intermediate connector can secure at least one end of the sheath. In certain embodiments, the intermediate connector can connect the first and second segments electrically and pneumatically. The sheath may overlay the intermediate connector.

In some embodiments, the segment proximate the patient is more flexible. The first segment and the second segment of the breathing tube can be composite tubes. The composite tube can have a first elongate member and a second elongate member. The first elongate member can include a hollow body spirally wound to form at least in part of the breathing tube, and the second elongate member can be spirally wound and joined between adjacent turns of the first elongate member. The second elongate member can form at least a portion of the lumen of the breathing tube.

In certain embodiments, a cross sectional width and height of the first elongate member of the more flexible segment are narrower and taller, respectively, than a cross sectional width and height of the first elongate member of the less flexible segment. The more flexible segment can have various modifications that can provide for more flexibility relative to the stiffer segment. Some example modification can include one or more of a smaller inner diameter, a smaller pitch, a smaller second elongate member width, or a thinner sidewall. The more flexible segment can have a thinner sidewall at a lumen than the more rigid segment. In certain embodiments, the first elongate member of the more flexible segment includes a sidewall proximate the gases lumen which is thinner than a sidewall proximate the gases lumen of the first elongate member of the less flexible segment.

In some embodiments, the breathing tube is an inspiratory tube in a breathing circuit. The breathing tube can be sized for use with neonates. The breathing tube can include a humidifier end adapted to connect to a humidifier. The breathing tube can include a patient end adapted to connect to a patient interface or wye piece.

Another embodiment provides for a breathing tube that includes a first segment of the breathing tube having a first flexibility and a sheath. The sheath can overlay the first segment. The sheath can be configured to maintain flexibility and dampen displacement during gas flow through the breathing tube. In certain embodiments, the breathing tube can include a second segment having a second flexibility and an intermediate connector. The intermediate connector can connect the first segment to the second segment. In certain embodiments, the flexibility of the second segment can be the same as the flexibility of the first segment. In other embodiments, the flexibility of the second segment can be the different than the flexibility of the first segment In certain embodiments, the intermediate connector can secure at least one end of the sheath. The sheath can be around at least one of the first segment or the second segment. The sheath can extend at least a partial length of the first and/or second segment. In certain embodiments, the sheath is around at least one of the first segment or the second segment and extends substantially along a whole length of the first and/or second segment. The sheath can extend around at least partially the length of each of the first segment and the second segment.

In some embodiments, the first segment and the second segment of the breathing tube can be composite tubes. The composite tube can have a first elongate member and a second elongate member. The first elongate member can include a hollow body spirally wound to form at least in part of the breathing tube, and the second elongate member can be spirally wound and joined between adjacent turns of the first elongate member. The second elongate member can form at least a portion of the lumen of the breathing tube. In certain embodiments, a cross sectional width and height of the first elongate member of the more flexible segment are narrower and taller, respectively, than a cross sectional width and height of the first elongate member of the less flexible segment. The more flexible segment can have various modifications that can provide for more flexibility relative to the stiffer segment. Some example modification can include one or more of a smaller inner diameter, a smaller pitch, a smaller second elongate member width, or a thinner sidewall. The more flexible segment can have a thinner sidewall at a lumen than the more rigid segment. In certain embodiments, the first elongate member of the more flexible segment includes a sidewall proximate the gases lumen which is thinner than a sidewall proximate the gases lumen of the first elongate member of the less flexible segment.

Another embodiment provides for a breathing tube that includes a humidifier end segment having a first flexibility and a patient interface end segment having a second flexibility. The second flexibility of the patient interface end segment is the same as the first flexibility of the humidifier end segment. A sheath can overlay the humidifier end segment. The sheath is configured to maintain flexibility and dampen displacement during gas flow. In some embodiments, the breathing tube can further include an intermediate connector connecting the humidifier end segment to the patient interface end segment. The intermediate connector secures at least one end of the sheath. The sheath can extend at least a partial length of the humidifier end segment. In certain embodiments, the sheath can extend substantially along the whole length of the humidifier end segment. In some embodiments sheath is around the humidifier end segment and the patient interface end segment. The sheath can extend at least a partial length of each segment.

In some embodiments, the humidifier end segment and the patient interface end segment of the breathing tube can be composite tubes. The composite tube can have a first elongate member and a second elongate member. The first elongate member can include a hollow body spirally wound to form at least in part of the breathing tube, and the second elongate member can be spirally wound and joined between adjacent turns of the first elongate member. The second elongate member can form at least a portion of the lumen of the breathing tube.

Some embodiments provide for a circuit kit for a humidified medical gas. The circuit kit can include a humidification chamber, and an inspiratory limb. The inspiratory limb can include a first segment of the breathing tube having a first flexibility, and a second segment of the breathing tube having a second flexibility, wherein the second flexibility is different than the first flexibility.

In some embodiments, the circuit kit can include a wye piece. The circuit kit may include an expiratory limb. The circuit kit may include a patient interface. The circuit kit may include an intermediate connector connecting the first segment to the second segment. The circuit kit may include a sheath around at least one of the first segment or the second segment. The circuit kit may include a dry line Some embodiments provide for a breathing tube. The breathing tube may include a first segment of the breathing tube having a first flexibility, a second segment of the breathing tube having a second flexibility, and a segment connector adapted to connect the first segment to the second segment. The segment connector can include a connection circuit configured to selectively provide power delivered to conductive filaments of the first segment to conductive filaments of the second segment.

In some embodiments, the connection circuit may include a diode. The diode may prevent power of a first polarity that is delivered to the conductive filaments of the first segment from being delivered to the conductive filaments of the second segment. The diode may allow power of a second polarity that is delivered to the conductive filaments of the first segment to be delivered to the conductive filaments of the second segment.

In some embodiments, the connection circuit may be configured to provide power to the conductive filaments of the first segment without providing power to the conductive filaments of the second segment in a first mode, and the connection circuit may be configured to provide power to both the conductive filaments of the first segment and the conductive filaments of the second segment in a second mode.

In some embodiments of the breathing tube, the second flexibility is the same as the first flexibility. In some embodiments of the breathing tube, the second flexibility is the different than the first flexibility. In some embodiments, the breathing tube may include a sheath around at least one of the first segment or the second segment. The intermediate connector may secure at least one end of the sheath.

In some embodiments, control of conductive filaments and reading of the sensors can be accomplished using less than four wires in each segment (e.g., using 3 wires or using 2 wires) or using more than four wires in each segment (e.g., using 5 wires, using 6 wires, using 7 wires, using 8 wires, or using more than 8 wires).

For purposes of summarizing the invention, certain aspects, advantages and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

Example embodiments that implement the various features of the disclosed systems and methods will now be described with reference to the drawings. The drawings and the associated descriptions are provided to illustrate embodiments and not to limit the scope of the disclosure.

FIGS. 2F and 2G illustrate an example printed circuit board ("PCB") of an intermediate connector.

FIGS. 2H and 2I illustrate example embodiments of intermediate connectors.

Figure 1:
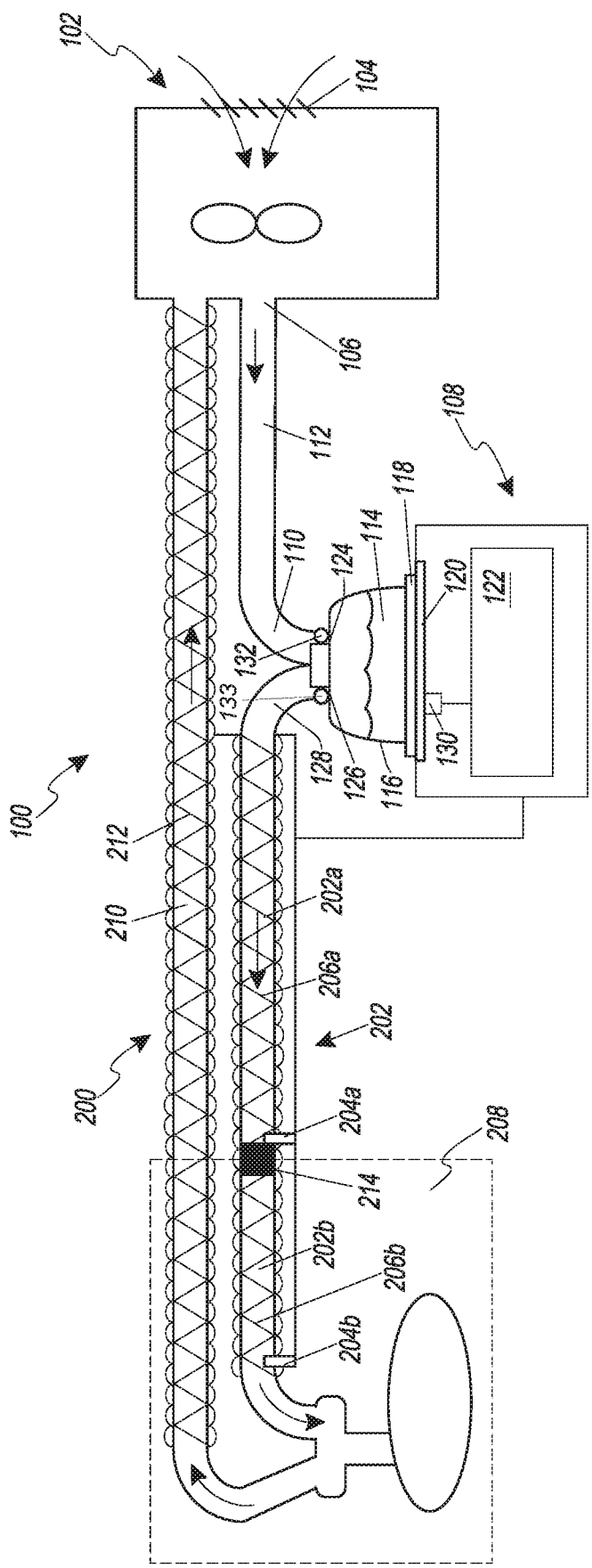
FIG. 1 illustrates an example respiratory humidification system for delivering humidified gas to a user, the respiratory humidification system having a breathing circuit that includes a segmented inspiratory limb with sensors in each segment.

Generally throughout the drawings, reference numbers are reused to indicate correspondence between referenced (or similar) elements. Nevertheless, corresponding referenced (or similar) elements may have different reference numbers in some circumstances.

DETAILED DESCRIPTION

Details regarding several illustrative embodiments for implementing the apparatuses and methods described herein are described below with reference to the figures. The invention is not limited to these described embodiments.

Certain embodiments and examples of segmented inspiratory limbs and multiple-zone heating are described herein. Those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described herein.

Described herein are systems and methods for providing heat to a segmented inspiratory limb in a breathing circuit of a respiratory humidification system. It will be understood that although much of the description herein is in the context of segmented inspiratory limbs in breathing circuits, one or more features of the present disclosure can also be implemented in other scenarios where it is desirable to provide differential heating in segmented gas delivery conduits such as in respiratory, surgical, or other applications.

The disclosure references heater wires, heating elements, heating filaments, and/or heaters in the context of providing heat to a conduit. Heater wire, for example, is a broad term and is to be given its ordinary and customary meaning to a person of ordinary skill in the art (that is, it is not to be limited to a special or customized meaning) and includes, without limitation, heater strips, heating filaments, and/or conductive elements that produce heat when electrical power is provided. Examples of such heating elements include wires made of a conductive metal (e.g., copper), conductive polymers, conductive inks printed on a surface of a conduit, conductive materials used to create a track on a conduit, and the like. Furthermore, the disclosure references conduits, limbs, and medical tubes in the context of gas delivery. Tube, for example, is a broad term and is to be given its ordinary and customary meaning to a person of ordinary skill in the art and includes, without limitation, passageways having a variety of cross-sections such as cylindrical and non-cylindrical passageways. Certain embodiments may incorporate a composite tube, which may generally be defined as a tube comprising two or more portions, or, specifically, in some embodiments, two or more components, as described in greater detail below. The segmented limbs comprising the disclosed medical tubes can also be used in breathing circuits such as a continuous, variable, or bi-level positive airway pressure (PAP) system, high flow delivery, invasive ventilation, non-invasive ventilation, high flow during anesthesia or sedated procedures, or other form of respiratory therapy. The terms conduit and limb should be construed in a manner that is similar to tube.

When a heated, humidified breathing tube is used for an incubator (or any region where there is a temperature change, such as around radiant warmers used for burn victims, or under a blanket used by a patient), the breathing tube will pass through at least two distinct zones: a lower temperature zone (such as the one outside the incubator) and a higher temperature zone (such as the one inside the incubator). If the tube is heated along its full length, one of the zones will tend to be at an undesirable, unsuitable, or non-optimal temperature, depending on which zone is sensed (e.g., which zone contains a temperature sensor). If the heater wire is controlled to a sensor inside the incubator (such as to a patient-end temperature sensor), the section outside the incubator will tend to be too cool, which can lead to condensation. Conversely, if the heater wire is controlled to a sensor outside the incubator, the section inside the incubator will tend to be too hot, which can lead to overheated gas being provided to the patient. Accordingly, the present disclosure describes systems and methods that provide for control over heat in a segmented breathing tube wherein each segment has an associated sensor providing feedback to a control module. Although several embodiments are described herein with respect to two zones, such a system could also be extended to apply to uses with additional zones, segments, or regions. For example, in an embodiment comprising three temperature zones, segments of the breathing tube may be heated based at least in part on three different temperature sensors in the zones. Furthermore, the embodiments disclosed herein can control the heat delivered to a breathing tube based on a parameter at the patient-end, bypassing or ignoring one or more of the sensors at intermediate points along the tube. Moreover, the embodiments disclosed herein can control the heat delivered to a breathing tube using parameters provided by sensors including, for example and without limitation, temperature sensors, humidity sensors, flow sensors, oxygen sensors, and the like.

A control module can monitor and control the heating temperatures in multiple zones or sections. The control module can be configured to provide heat to a first section of the breathing tube in a first mode and to the entire breathing tube in a second mode using embodiments of connector assemblies described herein. The embodiments described herein can be used without flying leads, exposed connectors, and/or patient-end electrical connections. Flying leads as used herein include electrical connections that extend externally of the breathing tubes, internally through the breathing tubes, and incorporated, molded, or otherwise formed or included as part of the breathing tubes. The control module can be located within the humidifier or externally to it. In some embodiments, the controller is located within the humidifier to control the heater wires associated with a first segment of an inspiratory limb, a second segment of an inspiratory limb, and an expiratory limb as well as read parameters from sensors associated with the first and second segments of the inspiratory limb and/or the expiratory limb.

The control module can also adaptively change the temperature for the segments. For example, the control module can monitor temperature sensors associated with one or more segments. The monitoring can be continuous, based on intervals, or other schemes such as interrupt or event-based monitoring. For example, the monitoring of temperature sensors can be based on reading values from an analog to digital converter, determining a voltage or current, sensing a logic condition, reading thermostatic devices, measuring thermistor values, measuring resistance temperature detectors, measuring the voltage of a thermocouple, or other methods for sensing temperature, including, but not limited to the use of semiconductor junction sensor, infrared or thermal radiation sensors, thermometers, indicators, or the like. In some embodiments, the temperature sensors are thermistors. The monitoring may be based on power signals such as, for example, measurement frequency of the sensors may be synchronous or asynchronous with the power signal frequency.

In some embodiments, the ratio of the power delivered to the first segment of the inspiratory limb and the second segment of the inspiratory limb can change during use based at least in part on feedback from sensors associated with each segment. For example, the ratio of power can be changed in a manner such that each segment is heated to a temperature to reduce or eliminate condensation. As a further example, the ratio of power can be changed so that overheated gas is not provided to the patient. In some embodiments, the ratio of power can be continuously changed based on feedback from sensors (e.g., temperature sensors, humidity sensors, oxygen sensors, flow sensors, optical sensors, etc.). The ratio of power can be changed in different ways. For example, the ratio of power can be changed by altering the amplitude of a power signal (including, without limitation, the voltage and/or current), the duration of the power signal, the duty cycle of the power signal, or other suitable changes to the power signal. In an embodiment, the ratio of power is changed by altering the magnitude of the current provided.

Respiratory Humidification Systems

FIG. 1 illustrates an example respiratory humidification system 100 for delivering humidified gas to a user, the respiratory humidification system 100 having a breathing circuit 200 that includes a segmented inspiratory limb 202 with sensor 204b in one segment, and which may optionally include sensor 204a in another segment. The segmented inspiratory limb 202 can be used in conjunction with an incubator 208, as illustrated, or with another system where there are different temperatures along different segments of the inspiratory limb 202, such as in conjunction with a radiant warmer. The segmented inspiratory limb 202 can be used to provide different levels of heat to different segments of the inspiratory limb 202a, 202b to reduce or prevent condensation and/or to control a temperature of gas delivered to a user. In some embodiments, inspiratory limb 202 is not segmented.

The illustrated respiratory humidification system 100 comprises a pressurized gas source 102. In some implementations, the pressurized gas source 102 comprises a fan, blower, or the like. In some implementations, the pressurized gas source 102 comprises a ventilator or other positive pressure generating device. The pressurized gas source 102 comprises an inlet 104 and an outlet 106. In some embodiments, the pressurized gas source 102 may be a wall gas source. In such embodiments, the gas from the wall may pass through a flow control valve, such as a flow meter or a blender or a proportional valve, that can be used to control the flow rate delivered to the patient.

The pressurized gas source 102 provides a flow of fluid (e.g., oxygen, anesthetic gases, air or the like, and/or a mixture of any such fluids) to a humidification unit 108. The fluid flow passes from the outlet 106 of the pressurized gas source 102 to an inlet 110 of the humidification unit 108. In the illustrated configuration, the humidification unit 108 is shown separate of the pressurized gas source 102 with the inlet 110 of the humidification unit 108 connected to the outlet 106 of the pressurized gas source 102 with a conduit 112 (sometimes referred to as a "dry line"). In some implementations, the pressurized gas source 102 and the humidification unit 108 can be integrated into a single housing.

While other types of humidification units can be used with certain features, aspects, and advantages described in the present disclosure, the illustrated humidification unit 108 is a pass-over humidifier that comprises a humidification chamber 114 and an inlet 110 to the humidification chamber 114. In some implementations, the humidification chamber 114 comprises a body 116 having a base 118 attached thereto. A compartment can be defined within the humidification chamber 116 that is adapted to hold a volume of liquid that can be heated by heat conducted or provided through the base 118. In some implementations, the base 118 is adapted to contact a heater plate 120. The heater plate 120 can be controlled through a controller 122 or other suitable component such that the heat transferred into the liquid can be varied and controlled.

The controller 122 of the humidification unit 108 can control operation of various components of the respiratory humidification system 100. While the illustrated system is illustrated as using a single controller 122, multiple controllers can be used in other configurations. The multiple controllers can communicate or can provide separate functions and, therefore, the controllers need not communicate. In some implementations, the controller 122 may comprise a microprocessor, a processor, or logic circuitry with associated memory or storage that contains software code for a computer program. In such implementations, the controller 122 can control operation of the respiratory humidification system 100 in accordance with instructions, such as contained within the computer program, and also in response to internal or external inputs. The controller 122, or at least one of the multiple controllers, can be located with the breathing circuit, either attached to the breathing circuit or integrated as part of the breathing circuit.

The body 116 of the humidification chamber 114 comprises a port 124 that defines the inlet 110, and a port 126 that defines an outlet 128 of the humidification chamber 114. As liquid contained within the humidification chamber 114 is heated, liquid vapor is mixed with gases introduced into the humidification chamber 114 through the inlet port 124. The mixture of gases and vapor exits the humidification chamber 114 through the outlet port 126.

The respiratory humidification system 100 includes a breathing circuit 200 comprising the inspiratory limb 202 connected to the outlet 128 that defines the outlet port 126 of the humidification unit 108. The inspiratory limb 202 conveys toward a user the mixture of gases and water vapor that exits the humidification chamber 114. The inspiratory limb 202 can include a heating element 206 positioned along the inspiratory limb 202, wherein the heating element 206 is configured to reduce condensation along the inspiratory limb 202, to control a temperature of gas arriving at the user, to maintain humidity of the gas, or any combination of these. The heating element 206 can raise or maintain the temperature of the gases and water vapor mixture being conveyed by the inspiratory limb 202. In some implementations, the heating element 206 can be a wire that defines a resistance heater. By increasing or maintaining the temperature of the gases and water vapor mixture leaving the humidification chamber 114, the water vapor is less likely to condensate out of the mixture.

The respiratory humidification system 100 optionally can be used in conjunction with an incubator 208. The incubator 208 can be configured to maintain a desired environment for a user within the incubator 208, such as a selected, defined, or desired temperature. Within the incubator 208, therefore, an interior ambient temperature may be different than a temperature outside the incubator 208. Thus, the incubator 208 causes, defines, creates, or maintains different temperature zones along the inspiratory limb 202, where the interior temperature is typically hotter than the exterior temperature.

Having at least two different temperature zones along the inspiratory limb 202 can create problems during delivery of gas to a user such as condensation along the inspiratory limb 202, delivering a gas that has a temperature that is too high, or both.

The respiratory humidification system 100 can include an expiratory limb 210 with associated heating element 212. In some embodiments, the expiratory limb 210 and the inspiratory limb 202 can be connected using a suitable fitting (e.g., a wye-piece). In some embodiments, the respiratory humidification system 100 can be used in conjunction with a radiant warmer, under a blanket, or in other systems or situations that create two or more temperature zones. The systems and methods described herein can be used with such systems and are not limited to implementations incorporating incubators.

In an example embodiment in which the limb is used with an incubator, the inspiratory limb 202 can be divided into segments 202a and 202b where a first segment 202a can be a portion of the inspiratory limb 202 that is outside the incubator 208 and a second segment 202b (e.g., an incubator extension), can be a portion of the inspiratory limb 202 that is inside the incubator 208. In other example embodiments where the limb is not used with an incubator, the tube can be segmented as described above, with both segments in the same or similar ambient conditions, or with the segments in different ambient conditions (for instance, where there might be a fan or HVAC/AC system blowing on one of the segments but not on the other). The first and second segments 202a, 202b can be different lengths or the same length. In some embodiments, the second segment 202b can be shorter than the first segment 202a, and, in certain implementations, the second segment 202b can be about half as long as the first segment 202a. The first segment 202a, for example, can have a length that is at least about 0.5 m and/or less than or equal to about 2 m, at least about 0.7 m and/or less than or equal to about 1.8 m, at least about 0.9 m and/or less than or equal to about 1.5 m, or at least about 1 m and/or less than or equal to about 1.2 m. The second segment 202b, for example, can have a length that is at least about 0.2 m and/or less than or equal to about 1.5 m, at least about 0.3 m and/or less than or equal to about 1 m, at least about 0.4 m and/or less than or equal to about 0.8 m, or at least about 0.5 m and/or less than or equal to about 0.7 m. In one example embodiment, the total length is greater than 2.5 m.

The segments of the inspiratory limb 202a, 202b can be coupled to one another to form a single conduit for gas delivery. In some embodiments, the first segment 202a can include one or more first heater wires 206a, may optionally include one or more first sensors 204a, and can be used without the second segment 202b. The controller 122 can be configured to control the first heater wires 206a and (if present) read the first sensor 204a without the second segment 202b being coupled to the first segment 202a. Furthermore, when the second segment 202b is coupled to the first segment 202a, the controller 122 can be configured to control the first and second heater wires 206a, 206b and read the first sensor 204a (if present) and second sensor 204b in their respective segments. In some embodiments, the controller 122 can be configured to control the respective first and second heater wires 206a, 206b and to read the respective first sensor 204a (if present) and the second sensor 204b when the second segment 202b is attached; and to control the first heater wires 206a and (if present) to read the first sensor 204a when the second segment 202b is not attached, without modification to the controller 122 or humidification unit 108. Thus, the same controller 122 and/or humidification unit 108 can be used whether the inspiratory limb 202 includes both the first and second segments 202a, 202b or only the first segment 202a. For instance, the same controller 122 and/or humidification unit 108 can be used where the inspiratory limb is a single segment inspiratory limb (i.e., not multiple segments), a sensor 204b at the patient end. In some embodiments, the controller 122 can be further configured to control the heater wires 212 in the expiratory limb 210 without modification to the controller 122 or humidification unit 108. Accordingly, the respiratory humidification system 100 can function with or without the second segment 202b attached and/or with or without the expiratory limb 210 attached. In one example embodiment, the expiratory limb control is a slave controller to the inspiratory limb heater wire controller. Alternatively the expiratory limb heater wires can be controlled independently of the inspiratory limb heater wires.

In some embodiments, the first and second segments 202a, 202b are permanently joined together to form a single conduit for gas delivery. As used here, permanently joined can mean that the segments 202a, 202b are joined together in a manner that makes it difficult to separate the segments, such as through the use of adhesives, friction fits, overmolding, mechanical connectors, and the like. In some embodiments, the first and second segments 202a, 202b are configured to be releasably coupled. For example, the first segment 202a can be used for gas delivery without the second segment 202b, or the first and second segments 202a, 202b can be coupled together to form a single conduit for gas delivery. In some embodiments, the first and second segments 202a, 202b can be configured such that they can be coupled together in only one configuration. For example, the first segment 202a can have a defined chamber-end (e.g., an end closest to the chamber 114 or humidification unit 108 along a direction of the flow of the humidified gas to the patient) and a defined patient-end (e.g., an end closest to the patient along a direction of the flow of the humidified gas to the patient) wherein the chamber-end is configured to couple to components at the chamber 114 and/or humidification unit 108. The second segment 202b can have a defined chamber-end and a defined-patient end wherein the chamber-end is configured to only couple to the patient-end of the first segment 202a. The chamber-end of the first segment 202a can be configured to not couple with either end of the second segment 202b. Similarly, the patient-end of the first segment 202a can be configured to not couple with the patient-end of the second segment 202b. Similarly, the patient-end of the second segment 202b can be configured to not couple with either end of the first segment 202a. Accordingly, the first and second segments 202a, 202b can be configured to be coupled in only one way to form a single conduit for gas delivery. In some embodiments, the first and second segments 202a, 202b can be configured to be coupled in a variety of configurations. For example, the first and second segments 202a, 202b can be configured to not include a defined patient-end and/or a defined chamber-end. As another example, the first and second segments 202a, 202b can be configured such that the patient-end and/or the chamber-end of the first segment 202a can couple to either the chamber-end or the patient-end of the second segment 202b. Similarly, the first and second segments 202a, 202b can be configured such that the chamber-end and/or the patient-end of the second segment 202a can couple to either the chamber-end or the patient-end of the second segment 202b.

The respiratory humidification system 100 can include an intermediate connector 214 that can be configured to electrically couple elements of the first and second segments 202a, 202b of the inspiratory limb 202. The intermediate connector 214 can be configured to electrically couple the heater wires 206a in the first segment 202a to the heater wires 206b in the second segment 202b to enable control of the heater wires 206a, 206b using the controller 122. The intermediate connector 214 can be configured to electrically couple the second sensor 204b in the second segment 202b to the first sensor 204a in the first segment to enable the controller 122 to acquire their respective outputs. The intermediate connector 214 can include electrical components that enable selective control of the heater wires 206a, 206b and/or selective reading of the sensors 204a, 204b. For example, the intermediate connector 214 can include electrical components that direct power through the first heater wires 206a in a first mode and through the first and second heater wires 206a, 206b in a second mode. The electrical components included on the intermediate connector 214 can include, for example and without limitation, resistors, diodes, transistors, relays, rectifiers, switches, capacitors, inductors, integrated circuits, micro-controllers, microprocessors, RFID chips, wireless communication sensors, optical sensors, and the like. In some embodiments, the intermediate connector 214 can be configured to be internal to the inspiratory limb 202 such that it is substantially shielded from external elements (e.g., less than 1% of the water, particulates, contaminates, etc. from an environment external to the inspiratory limb 202 contacts the intermediate connector 214). In some embodiments, some of the electrical components on the intermediate connector 214 can be configured to be physically isolated from the humidified gas within the inspiratory limb 202 to reduce or prevent damage that may result from exposure to humidity. In some embodiments, the intermediate connector 214 can include relatively inexpensive passive electrical components to reduce cost and/or increase reliability.

The inspiratory limb 202 may include sensor 204b, and may optionally include sensor 204a, in respective segments of the inspiratory limb 202b, 202a. The first sensor 204a may be positioned near an end of the first segment 202a, close to the incubator 208 so that the parameter derived from the first sensor 204a corresponds to a parameter of the humidified gas entering the second segment 202b. The second sensor 204b may be positioned near an end of the second segment 202b so that the parameter derived from the second sensor 204b corresponds to a parameter of the humidified gas delivered to the patient or user. The output of the sensors 204a (if present), 204b can be sent to the controller 122 as feedback for use in controlling power delivered to the heating elements 206a, 206b of the segments of the inspiratory limb 202a, 202b. In some embodiments, one or both of the sensors 204a, 204b can be temperature sensors, humidity sensors, oxygen or gas concentration/composition sensors, flow sensors, pressure sensors, or the like. A temperature sensor can be any suitable type of temperature sensor including, for example and without limitation, a thermistor, thermocouple, digital temperature sensor, transistor, and the like. The parameters provided by or derived from the sensors can include, for example and without limitation, temperature, humidity, oxygen content, flow rate, or any combination of these or the like.

The controller 122 can be configured to control the heater wires 206a and 206b, to receive feedback from the sensors 204a (if present) and/or 204b, to provide logic to control power to the heater wires 206a and 206b, to adjust control of the heater wires 206a and 206b in response to readings from the sensors 204a (if present) and/or 204b, to detect a presence of a second segment 202b of the inspiratory limb 202, to derive parameters from the readings from the sensors 204a (if present) and/or 204b, and the like. In some embodiments, the controller 122 includes a power source configured to deliver electrical power to the heater wires. The power source can be a source of alternating current or direct current. In some embodiments, the controller 122 can receive input from a heater plate sensor 130. The heater plate sensor 130 can provide the controller 122 with information regarding a temperature and/or power usage of the heater plate 120. In some embodiments, the controller 122 can receive input from one or more sensors 132. Any suitable sensor or sensors 132 can be used and the sensor(s) 132 can be positioned between ambient air and the humidification chamber 114 or between the pressurized gas source 102 and the humidification chamber 114. In the illustrated system, the sensor(s) 132 is positioned on the inlet port 124 of the humidification chamber 114. Sensor(s) 132 may sense one or more of flow, temperature, humidity, pressure, gas concentration or composition of the gases flow. In some embodiments, the controller 122 can receive input from one or more sensors 133. The one or more sensors 133 can be positioned at or near the outlet port 126 of the humidification chamber 114. The one or more sensors 133 can be temperature sensors, humidity sensors, oxygen sensors or gas concentration/composition sensors, flow sensors, pressure sensors, or the like. A temperature sensor can be any suitable type of temperature sensor including, for example and without limitation, a thermistor, thermocouple, digital temperature sensor, transistor, and the like. The parameters provided by or derived from the sensors can include, for example and without limitation, temperature, humidity, oxygen content or other gases composition/concentration, flow rate, pressure, or any combination of these or the like.

Any suitable patient interface can be incorporated. Patient interface is a broad term and is to be given its ordinary and customary meaning to a person of ordinary skill in the art (that is, it is not to be limited to a special or customized meaning) and includes, without limitation, masks (such as tracheal mask, face masks and nasal masks), nasal cannulas, surgical cannulas for laparoscopic or keyhole surgery, tracheostomy tubes or interfaces, and nasal pillows.

Segmented Inspiratory Limbs

Figure 2A:
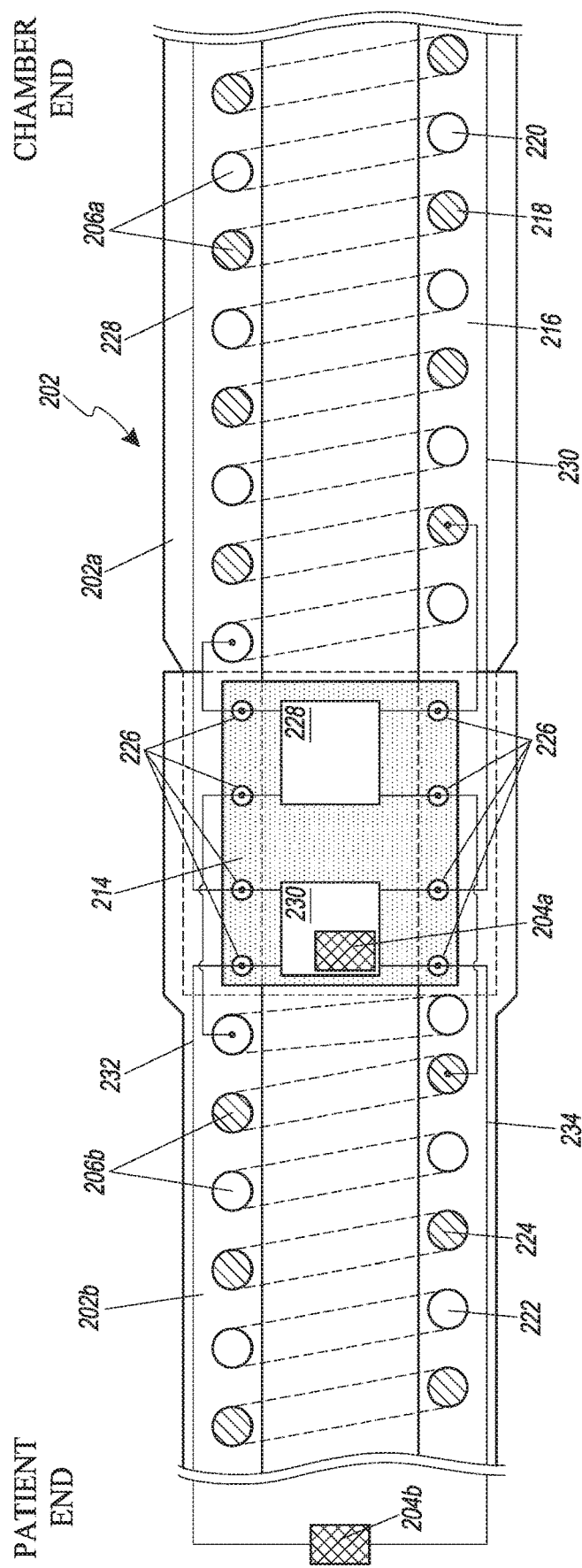
FIG. 2A illustrates a segmented inspiratory limb for use with a humidification system, the segmented inspiratory limb having an intermediate connector configured to couple heater wires and sensors in the two segments.

FIG. 2A illustrates a portion of a segmented inspiratory limb 202 for use with a respiratory humidification system 100, the segmented inspiratory limb 202 comprising a first segment 202a and a second segment 202b and having an intermediate connector 214 configured to couple first heater wires 206a to second heater wires 206b and, if present, a first sensor 204a to a second sensor 204b, in the respective segments 202a and 202b. Coupling the two segments 202a and 202b can comprise mechanically coupling the segments to form a single conduit through which humidified gases can be delivered to a user wherein mechanically coupling the segments 202a and 202b can result in electrically coupling the respective heater wires 206a, 206b and the respective sensors 204a (if present), 204b through the intermediate connector 214.

The segmented inspiratory limb 202 can comprise a structure 216 forming a lumen through which humidified gases can pass. The structure 216 can include paths formed within walls of the structure 216 configured to house heater wires 206a or 206b such that the heater wires 206a or 206b are shielded from the humidified gases travelling through the lumen and/or are covered by an external surface of the structure 216 so that they are not exposed. For example, the structure 216 can be a spiral composite tube wherein the heater wire paths are coils molded into the tube. The structure 216 can comprise any type of suitable material and can include insulating material and/or flexible material. In some embodiments, the structure 216 and the intermediate connector 214 can be configured such that, when the first and second segments 202a and 202b are mechanically coupled, the heater wires 206a and 206b wrap over the intermediate connector 214 in such a way as to be electrically coupled to the intermediate connector 214. In some embodiments, the first segment 202a and/or the intermediate connector 214 can exclude any flying leads for connecting to the second segment 202b, thereby facilitating connection of the second segment 202b to the first segment 202a.

The structure 216 at complementary ends of the first and second segments 202a and 202b can be configured to house the intermediate connector 214. Thus, the intermediate connector 214 can be internal to the inspiratory limb 202. In some embodiments, the complementary ends of the first and second segments 202a and 202b can be configured to shield the intermediate connector 214 from humidified gases travelling through the inspiratory limb 202. In some embodiments, the intermediate connector 214 is both internal to the inspiratory limb 202 and shielded from humidified gases in the conduit, thereby reducing or eliminating exposure of electrical connections on the intermediate connector 214.

In some embodiments, the first heater wires 206a can comprise two wires 218 and 220 and the second heater wires 206b can comprise two wires 222 and 224. The two wires 218 and 220 in the first segment 202a can be electrically coupled to one another through electrical components 228 wherein the electrical coupling creates an electrical path through the wire 218, at least a portion of the electrical components 228, and the wire 220. Similarly, the two wires 222 and 224 in the second segment 202b can be electrically coupled to one another through electrical components 228 and/or electrically shorted together at an end of the segment 202b opposite the intermediate connector 202b, such as through a patient-end connector (not shown) as described in greater detail herein with reference to FIGS. 3A, 3B, 8A, 8B, 9, and 13. By coupling the wires 222 and 224 of the second segment 202b at the intermediate connector 214, electrical connections at the patient-end of the inspiratory limb 202 are reduced or eliminated which can reduce cost, system complexity, and/or risk to the patient.

The intermediate connector 214 can be configured to allow a single controller to control power to the heater wires 206a, 206b, wherein the controller can be the humidifier controller 122 as described herein with reference to FIG. 1. In some embodiments, the humidifier controller 122 controls the heater wires without any additional control functionality located on the intermediate connector 214. For example, the intermediate connector 214 can include passive components without any logic circuitry wherein the passive components direct power to heater wires 206a and/or 206b as selected by the controller 122. This can allow the intermediate connector 214 to be designed using relatively inexpensive components and can reduce the complexity of the design.

In some embodiments, heating of the two segments 202a and 202b can be accomplished using a maximum of four wires in each segment 202a, 202b. For example, in the first segment 202a the four wires can include a first heater wire 218, a second heater wire 220, a signal sensor wire 228, and a return sensor wire 230. In the second segment 202b the four wires can include a first heater wire 222, a second heater wire 224, a signal sensor wire 232, and a return sensor wire 234. By coupling the second heater wires 222, 224 to the first heater wires 218, 220 at connection points 226, and by coupling the second sensor wires 232, 234 to the first sensor wires 228, 230 at connection points 226, a controller can be configured to provide power independently to the first heater wires 206a and the second heater wires 206b and to read sensor data independently from the sensors 204a (if present) and 204b without including more than four wires in either segment 202a or 202b. In some embodiments, control of the heater wires 206a and 206b and reading of the sensors 204a (if present) and 204b can be accomplished using less than four wires in each segment (e.g., using 3 wires or using 2 wires) or using more than four wires in each segment (e.g., using 5 wires, using 6 wires, using 7 wires, using 8 wires, or using more than 8 wires). In one example embodiment, there may be different numbers of wires in each segment, such that the segment with more wires is relatively less flexible than the segment with fewer wires. For example, segment 202a may include eight wires, while segment 202b may include only four wires. In this example, segment 202a would be relatively less flexible than segment 202b (which would be relatively more flexible). In another example embodiment the second elongate member may include a second and third elongate member (i.e. using two-start extrusion). Such second and third elongate members may be separated by successive first elongate member windings, or may be adjacent to each other between successive windings of the first elongate member. In this example embodiment, each of the second and third elongate members may include one wire, or more than one wire. In this way, one of skill in the art can be sure to provide adequate physical space for the wire(s) to ensure they are adequately insulated from each other so as not to spark or short.

The intermediate connector 214 can include electrical components 228 configured to allow a controller 122 to selectively control heater wires 206a, 206b. The controller 122 can be configured to control heating of the inspiratory limb 202 using two modes wherein a first control mode comprises providing power to the heater wires 206a in the first segment, and a second control mode comprises providing power to the heater wires 206a and 206b in the first and second segments 202a and 202b. Thus, the controller 122 can be configured to independently control heater wire sections. This ability allows for the controller 122 to control heating of the inspiratory limb 202 when the second segment 202b is not present by solely controlling the heating of the inspiratory limb according to the first control mode, thereby allowing for the respiratory humidification system 100 to be used in a variety of circumstances without modifying the controller 122 or humidification unit 108. In some embodiments, the control modes can include a mode where power is delivered only to the heater wires 206b in the second segment 202b. In some embodiments, the controller 122 includes an electrical power source that provides electrical current. The first and second control modes can be based at least in part on the voltage supplied by the power source wherein a positive voltage or positive current can trigger the first control mode and a negative voltage or a negative current can trigger the second control mode. In some embodiments, the power source provides rectified AC or DC power to the heater wires 206a, 206b and a change in the rectification or polarity triggers a change in the control mode. By switching control modes, control of heating in the breathing circuit 200 can be accomplished with any power supply that can switch the polarity of the output signal. In some embodiments, the amount of power provided to the heater wires 206a, 206b can be adjusted by adjusting a duty cycle of power applied to the heater wires 206a, 206b. For example, pulse-width modulation (PWM) can be used to power the heater wires 206a, 206b and the duty cycle of the PWM signal can be adjusted to control the power delivered. In another example, the amount of power provided to the heater wires 206a, 206b can be adjusted by controlling the amplitude of the power signal.

The intermediate connector 214 can include electrical components 230 configured to allow a controller 122 to selectively read sensors 204a (if present), 204b. Selective reading can be accomplished through the use of a source of electrical current wherein applying a positive current across the wires 228 to 230 can result in the controller 122 measuring a signal from the first sensor 204a and applying a negative current across the wires 228 and 230 can result in the controller 122 measuring a signal from the second sensor 204b or, if the first sensor 204a is present, from both the first and second sensors 204a, 204b. The controller 122 can use the readings from the sensors 204a (if present), 204b to adjust power to the heater wires 206a, 206b, using, for example pulse-width modulation. The first sensor 204a (if present) may be positioned near the connection or intersection of the first and second segments 202a and 202b to provide to the controller 122 a parameter of gases entering the second segment 202b, which can correspond to entering an incubator or other such region having a different ambient temperature. The second sensor 204b can be positioned at a patient-end of the second segment 202b to provide to the controller 122 a parameter of gases delivered to the patient or a parameter of gases prior to the final piece before the patient, such as a wye-piece. The controller 122 can use these readings to adjust power to the heater wires 206a, 206b to maintain the temperature of the gas at the patient-end of the inspiratory limb 202 at a targeted or suitable temperature. The targeted or suitable temperature can vary depending at least in part on the application and environment it is being used in, and can be about 37° C., about 40° C., at least about 37° C. and/or less than or equal to about 38° C., at least about 36.5° C. and/or less than or equal to about 38.5° C., at least about 36° C. and/or less than or equal to about 39° C., at least about 35° C. and/or less than or equal to about 40° C., at least about 37° C. and/or less than or equal to about 43° C., or at least about 39.5° C. and/or less than or equal to about 40.5° C. In some embodiments, the second sensor 204b can be positioned inside the incubator but not attached to the breathing circuit. By measuring parameters inside the incubator, the temperature of the second segment 202b can be calculated, for example.

The controller 122 can independently control the amount of power delivered in the first and second control modes, as described herein. Based at least in part on feedback from the sensors 204a (if present) and/or 204b, the controller 122 can independently adjust power delivered in the first and second control modes, thereby resulting in varying heater power ratios between the first and second segments 202a and 202b.

In some embodiments that include the first sensor 204a, the first sensor 204a is positioned within the flow of gas within the inspiratory limb 202. In some embodiments, the intermediate connector 214 or the first segment 202a can include a mechanical component that decreases turbulence in the flow of the gas across the first temperature sensor 204a which can increase accuracy in the readings of the sensor 204a. For example, the mechanical connector can have an aerodynamic cross section. In some embodiments, the mechanical component (e.g., a cross-member feature within the inspiratory conduit) that decreases turbulence also secures the sensor 204a within the flow of the gases. In some embodiments, the intermediate connector 214 and the mechanical component are configured to thermally isolate the sensor 204a from the electrical components on the intermediate connector 214, which may be advantageous where the sensor 204a is a temperature sensor, for example.

In some embodiments, the intermediate connector 214 includes additional connection points in addition to the connection points 26 illustrated in FIG. 2A. The additional connection points can be used to incorporate further functionality into the breathing circuit such as, for example, incorporating a memory device (PROM or flash memory or any other suitable type of memory), a micro-controller, additional circuits, and the like. In an alternative embodiment, the second segment may be removably coupled to the first segment via the intermediate connector. The intermediate connector may include a socket or region to receive a corresponding connector on the second segment. The connector on the second segment and intermediate connector can form electrical and pneumatic connections with the second segment, so as to join the first segment and the second segment via the intermediate connector.

Example Segmented Inspiratory Limb with a Connector having a Micro-controller

Figure 2B:
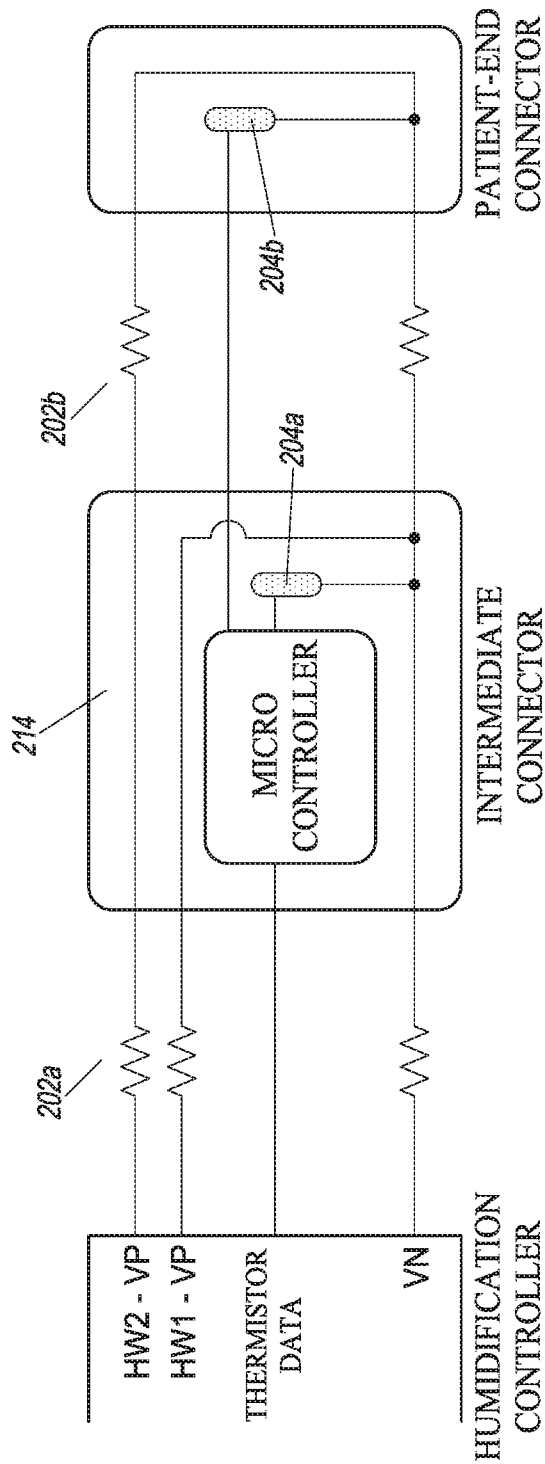
FIG. 2B illustrates an example embodiment of a humidification system that utilizes a micro-controller in an intermediate connector to measure data for controlling heating and to read sensor values in an inspiratory limb.

FIG. 2B illustrates an example embodiment of a respiratory humidification system 100 that utilizes a micro-controller in an intermediate connector 214 to measure data for controlling heating and to read sensor values in an inspiratory limb 202. In some embodiments, one or more micro-controllers can be incorporated in a sensor cartridge, in the humidifier, in the intermediate connector 214, or in any combination of these. The micro-controller provides similar functionality as described herein when incorporated on the sensor cartridge, for example. The illustrated example embodiment uses one heater wire as a common reference, the wire connected to VN, and connects the two heater wires HW1, HW2 and the sensor wires to the common reference. The example embodiment also converts both sensors' 204a, 204b readings into a digital signal in the intermediate connector 214 to send to the humidifier controller 122. This can reduce or eliminate isolation issues by referencing the sensors 204a (if present), 204b to a common reference point and by sending a digital parameter reading which can be passed through an optocoupler on the controller 122 which will isolate the signal, as described herein with reference to FIG. 2E. Using this example embodiment can allow for two independent channels of control to heat just the first section 202a or the first and second sections of the inspiratory limb 202a, 202b to provide a desired, selected, or defined heating control.

Figure 2C:
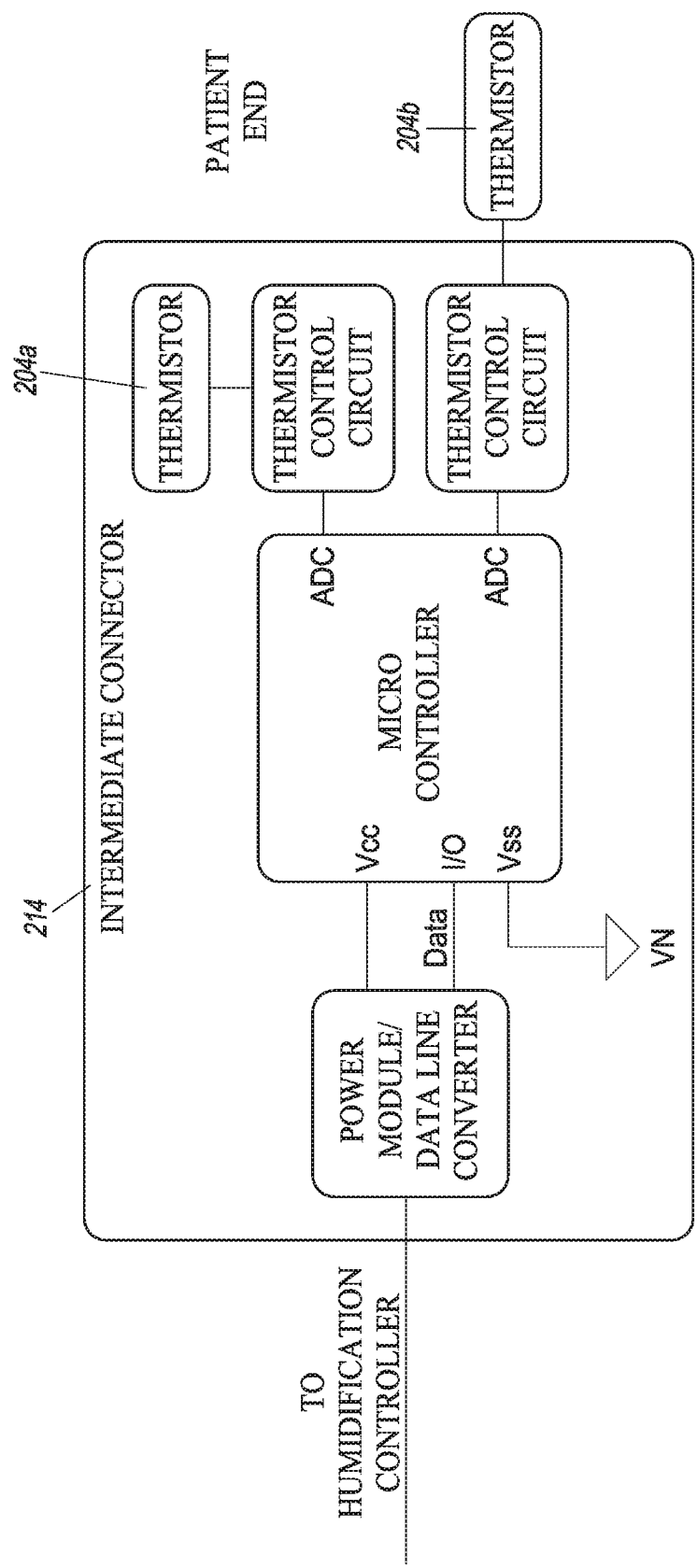
FIG. 2C illustrates a block diagram of an example intermediate connector for an inspiratory limb, wherein the intermediate connector uses a micro-controller.
Figure 2D:
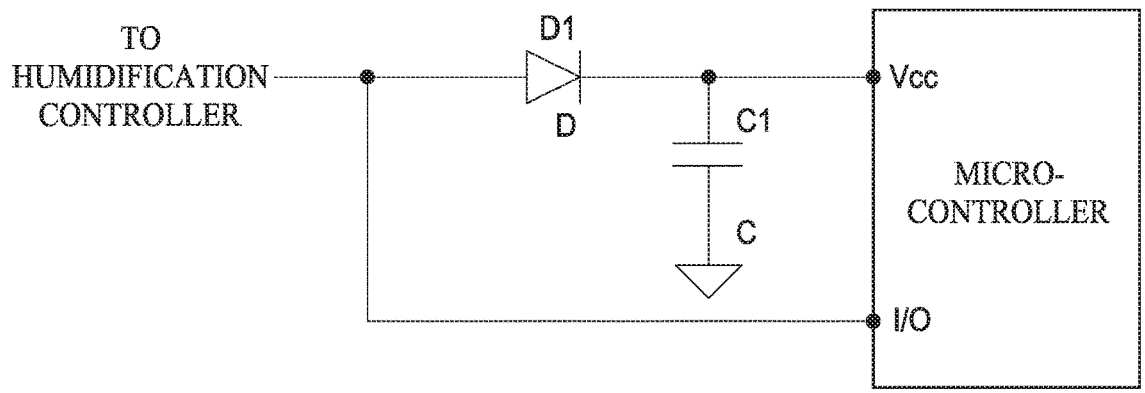
FIG. 2D illustrates a circuit diagram for an example power module and data line converter included in the intermediate connector illustrated in FIG. 2C.

FIG. 2C illustrates a block diagram of an intermediate connector 214 for an inspiratory limb 202, wherein the intermediate connector 214 uses a micro-controller. The micro-controller can be used to measure an analog signal from the thermistors 204a and 204b and convert the analog signal into a digital signal using analog-to-digital converters (ADCs). The converted digital signal can be sent to the humidifier controller 122 on a single data line. The data line can be used to allow communication between the micro-controller and the humidifier controller 122 to provide temperature data. The data line can be used to provide power to the micro-controller by pulling the data line high on the humidifier controller 122 when data is not being sent. The power module and data line converter can include a capacitor and a diode so that the capacitor is charged when the data line is high. The charged capacitor can be used to power the micro-controller when the data line is being used for communication. The circuit diagram for an example power module and data line converter is illustrated in FIG. 2D. In another example embodiment, the sensors 204a (if present), 204b may sense parameters other than temperature, such as flow rate, humidity, pressure, etc. In another example embodiment, the sensors 204a (if present), 204b are not thermistors but are some other sensing component, such as optical sensors, capacitive sensors, resistive sensors, or other conventional sensors as are known in the art.

Temperature sensing using this configuration can be accomplished using a current source or a voltage source on the intermediate connector 214 to drive the thermistors so they can be read by the micro-controller. This can be done using, for example, transistors or an op-amp. Data line communication can be accomplished using a time-slot based approach where each logic level can be sent and read in a predefined time slot. In this way, one wire can be used to allow two-way communication between the humidifier controller 122 and the micro-controller.

Figure 2E:
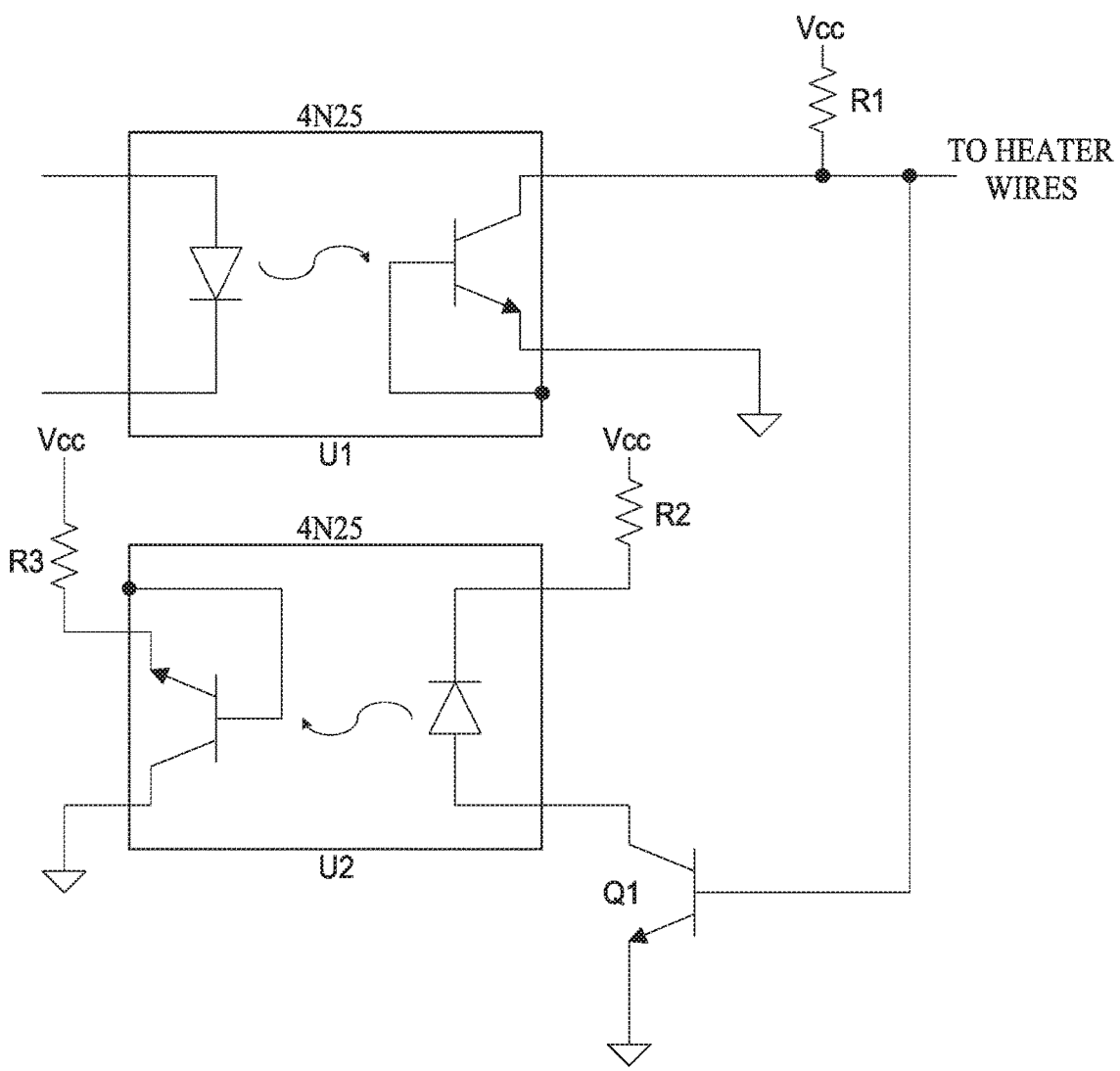
FIG. 2E illustrates a circuit diagram of an example dual optocoupler circuit used in conjunction with the intermediate connector illustrated in FIG. 2C to provide two-way data communication between a control side and an AC side on a power board.

The humidifier controller 122 can include a DC power supply that is referenced to VN. A capacitor can be included which can be charged when the heater wires are on and can provide power to the micro-controller while the heater wires are turned off. The humidifier controller 122 can include a dual optocoupler circuit 1200, as illustrated in FIG. 2E. The dual optocoupler circuit can be used to isolate signals and for two-way data communication between the controller 122 and a power supply.

In some embodiments, calibration data can be stored on the micro-controller which can be read when a breathing circuit is connected. In some embodiments, part identification numbers or serial numbers can be stored to determine an origin of a connected circuit.

Intermediate Connector Board

FIGS. 2F and 2G illustrate an example intermediate PCB 250 of the intermediate connector 214, the respective figures illustrating two sides of the intermediate PCB 250. The intermediate PCB 250 includes connection pads 252, 254 for the heater wires and sensor connections. The connection pads 252, 254 are configured to be on opposite sides of the intermediate PCB 250 to facilitate connections with heater wires wound spirally around an inspiratory limb.

The intermediate PCB 250 includes sensor connection pads 256 for the sensor, such as a thermistor or other temperature measurement component, or humidity sensor, or a flow sensor, or the like. The sensor can be coupled to a diode through signal connection pads 258 on the intermediate PCB 250. As illustrated, the intermediate PCB 250 includes a gap 262 configured to thermally insulate the sensor from the other electrical components and tracks. In some embodiments, the gap 262 can be filled with an insulating material to further thermally isolate the sensor connected to sensor connection pads 256. In addition, the intermediate PCB 250 can be configured to position the sensor apart from the other active and/or passive electrical components, such as with the protruding feature 257.

The intermediate PCB 250 includes power connection pad 260 for a diode electrically coupled to the heater wires through electrical tracks on the intermediate PCB 250. The diode can be the diode D1 described with reference to FIGS. 2K and 2M. The power connection pad 260 can be electrically and thermally coupled to heat sink 264 to aid in dissipating heat, to reduce or minimize effects on the accuracy of the parameter reading of the sensor coupled to the sensor connection pads 256.

FIGS. 2H and 2I illustrate example embodiments of intermediate connectors 214 comprising an intermediate PCB 250 and an intermediate connection element 263. The intermediate connection element 263 can be configured to direct a portion of the humidified gas flowing through an inspiratory limb through a conduit formed by the intermediate connection element 263. An optional sensor on the intermediate PCB 250 can then provide a signal corresponding to a parameter of the gas flowing through the intermediate connection element 263, the parameter being representative of at least one property (e.g., temperature, humidity, flow rate, oxygen percentage, etc.) of the humidified gas at that point in the inspiratory limb. In some embodiments, the intermediate connection element 263 is configured to provide mechanical support for the intermediate PCB 250, to position it within the inspiratory limb. In some embodiments, the intermediate connection element 263 is configured to provide mechanical support for joining two segments of an inspiratory limb together at or near the intermediate connector 214.

The intermediate connector 214 includes first connection pads 252 on a first side of the intermediate PCB 250 and second connection pads 254 on a second side of the intermediate PCB 250, the second side being on an opposite side of the intermediate PCB 250. The first and second connection pads 252, 254 can be configured to provide electrical contacts for heater wires in respective first and second segments of a segmented inspiratory limb, as described herein. In some embodiments, heater wires in a segment of an inspiratory limb are spirally wound. The intermediate PCB 250 is configured to electrically couple spirally-wound heater wires and/or signal wires (e.g., temperature sensor wires) in a first segment to spirally-wound heater wires and/or signal wires in a second segment.

In some embodiments, the intermediate PCB 250 includes a first portion extending across a lumen formed by the intermediate connection element 263 along a diameter or chord line, such that a portion of the intermediate PCB 250 generally bisects at least part of the flow path of the gas. The first portion of the intermediate PCB 250 can be overmolded by an overmolding composition. The intermediate PCB 250 can include a second portion 251 adjacent the first portion projecting outward from an exterior of the intermediate connection element 263 in a direction away from the lumen. The second portion 251 of the intermediate PCB 250 includes one or more connection pads 252 configured to receive one or more wires from a first segment of the inspiratory limb. The intermediate PCB 250 can include a third portion 253 adjacent the first portion projecting outward from the exterior of the intermediate connection element 263 in a direction away from the lumen and in a direction opposite the second portion 251. The third portion 253 can include one or more connection pads 254 on the intermediate PCB 250 configured to receive one or more wires from a second segment of the inspiratory limb. The intermediate PCB 250 can include one or more conductive tracks configured to electrically couple the one or more connection pads 252 of the second portion 251 to the one or more connection pads 254 of the third portion 253 and configured to provide an electrical connection between the wires in the first segment and the wires in the second segment of the inspiratory limb.

Intermediate Connector Circuits

Figure 2J:
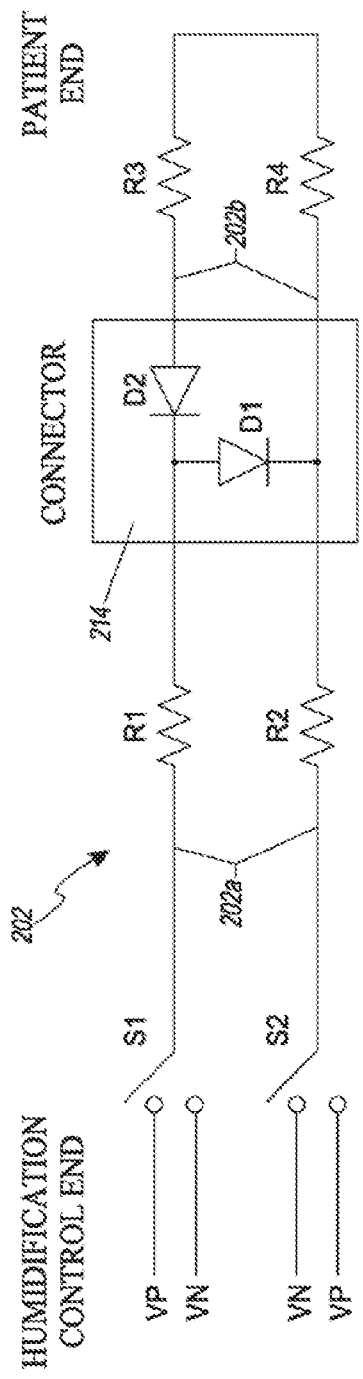
FIGS. 2J and 2K illustrate example circuit diagrams including an active rectified power source for providing power to heater wires in a segmented inspiratory limb of a breathing circuit, wherein the circuit is configured to power heater wires in a first segment of the inspiratory limb in a first mode and to power heater wires in both segments in a second mode.

FIG. 2J illustrates a circuit diagram of an example intermediate connector 214 including an active rectified power source for providing power to heater wires in a segmented inspiratory limb of a breathing circuit, wherein the circuit is configured to power heater wires R1 and R2 in a first segment of the inspiratory limb in a first mode and to power heater wires R1, R2, R3, and R4 in both segments in a second mode. By providing diodes D1 and D2 on the intermediate connector 214 and switches S1 and S2, power can be alternatively applied through heater wires R1 and R2, where the resistors represent the heater wires, or through heater wires R1, R2, R3, and R4.

The power source is represented in the figure using VP and VN which correspond to terminals of a power supply. In an embodiment, the voltage supply is an alternating current (AC) power supply. Alternatively, the power source can be a direct current (DC) power supply. Although described in this embodiment as diodes, D1 and D2 can include any of a plurality of different types of flow control devices such as, for example and without limitation, rectifiers, transistors, relays, switches, triacs, mosfets, thyristors (SCR), thermostats, and the like.

The switches S1 and S2 switch between the VP and VN terminals of the power source. In an embodiment, switches S1 and S2 are switched every half-cycle of an AC power cycle so that approximately equal current is drawn from the power source during every half cycle. The circuit illustrated in FIG. 2B can be used to control the heaters R1, R2, R3, and R4 in two control modes, wherein a first control mode corresponds to providing power only to R1 and R2, and a second control mode corresponds to providing power to R1, R2, R3 and R4. To provide power only to the heaters R1 and R2 in the first segment 202a (corresponding to the first control mode), switch S1 connects to VP and switch S2 connects to VN during a positive cycle from the power source, and switch S1 connects to VN and switch S2 connects to VP during a negative cycle from the power source. In the first control mode, current flows through R1, R2, and D1 while D2 prevents current from flowing through R3 and R4. To provide power to the heaters R1, R2, R3, and R4 in the first and second segments 202a, 202b (corresponding to the second control mode), switch S1 connects to VN and switch S2 connects to VP during a positive cycle from the power source, and switch S1 connects to VP and switch S2 connects to VN during a negative cycle from the power source. In the second control mode, current flows through R1, R2, R3, R4, and D2 while D1 prevents current from shorting across the wires to bypass heaters R3 and R4. Switching of switches S1 and S2 can be accomplished through hardware or software that adds logic to the system. In some embodiments, switching of switches S1 and S2 is performed at the zero crossing of an AC power cycle. In some embodiments, the falling and rising edges of zero crossing circuitry are not delayed by the same amount and the circuit is not active near the zero crossing. Thus, the switching of switches S1 and S2 can be performed with or without zero-crossing switching detection and/or logic.

The diodes D1 and D2 can dissipate power in the circuit, and therefore generate heat. In some embodiments, Schottky diodes can be used where it is desirable to reduce power dissipation in relatively high-temperature environments. Schottky diodes can be operated near a maximum junction temperature to reduce or minimize power dissipation, which may be desirable in certain implementations of the respiratory humidification system described herein. In some embodiments, the heat generated by the diode can influence temperature readings of the sensor 204a (if present). To reduce this influence, the diodes can be thermally connected to an airflow path of the circuit. To reduce this influence and to dissipate the heat generated by the diodes, a heat sink or pad can be included on the intermediate connector 214 that is thermally coupled to the ambient environment. To reduce this influence, and the influence of other components on the intermediate connector 214, the sensor 204a (e.g., a thermistor or other temperature sensor) can be thermally insulated from the components and physically located relatively far from the other components, as described with reference to FIGS. 2F and 2G.

Figure 2K:
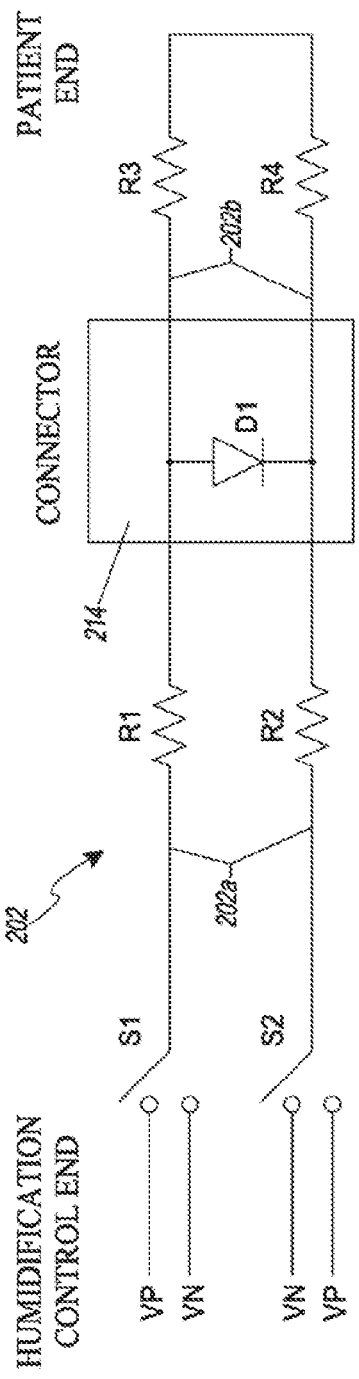

FIG. 2K illustrates another circuit diagram of an example intermediate connector 214 including an active rectified power source for providing power to heater wires in a segmented inspiratory limb of a breathing circuit, wherein the circuit is configured to power heater wires R1 and R2 in a first segment of the inspiratory limb in a first mode and to power heater wires R1, R2, R3, and R4 in both segments in a second mode. As shown in FIG. 2K, only diode D1 may be provided and the path of power through heater wires R1 and R2 or through heater wires R1 through R4 can still be controlled, as previously described with respect to FIG. 2J. The diode D2 that was shown in the circuit of FIG. 2J is eliminated. The circuit shown in FIG. 2K, having only one diode D1, can result in less heat generated by the circuit, reduced parts costs, and a smaller circuit board. The remaining portions of the circuit shown in FIG. 2K operate in a manner that is similar to the description of FIG. 2J. In embodiments without D2, as illustrated in FIG. 2K, most of the current flows through R1, R2 and D1 with only residual current flowing through R3 and R4. The residual current through R3 and R4 can be negligible such that it does not affect the performance of the humidification system.

In addition to the AC operation described with respect to FIGS. 2J and 2K, similar circuits can be operated with a DC supply. Switches S1 and S2 can be switched based at least in part on, for example, time, an output current of the supply, feedback from sensors, or other control inputs. In such an embodiment, the circuits illustrated in FIGS. 2J and 2K also can be used to control the heaters R1, R2, R3, and R4 in two control modes, wherein a first control mode corresponds to providing power only to R1 and R2, and a second control mode corresponds to providing power to R1 through R4. To provide power only to the heaters R1 and R2 in the first segment 202a (corresponding to the first control mode), switch S1 connects to VP and switch S2 connects to VN. In the first control mode, current flows through R1, R2, and D1. D2 prevents current from flowing through R3 and R4 in the circuit shown in FIG. 2J. However, D2 is an optional component as shown in FIG. 2K. To provide power to the heaters R1, R2, R3, and R4 in the first and second segments 202a, 202b (corresponding to the second control mode), switch S1 connects to VN and switch S2 connects to VP. In the second control mode, current flows through R1, R2, R3, R4, while D1 prevents current from shorting across the wires to bypass heaters R3 and R4. As previously described, switching can be accomplished through hardware or software that adds logic to the system.

Sensor Circuits

Figure 2L:
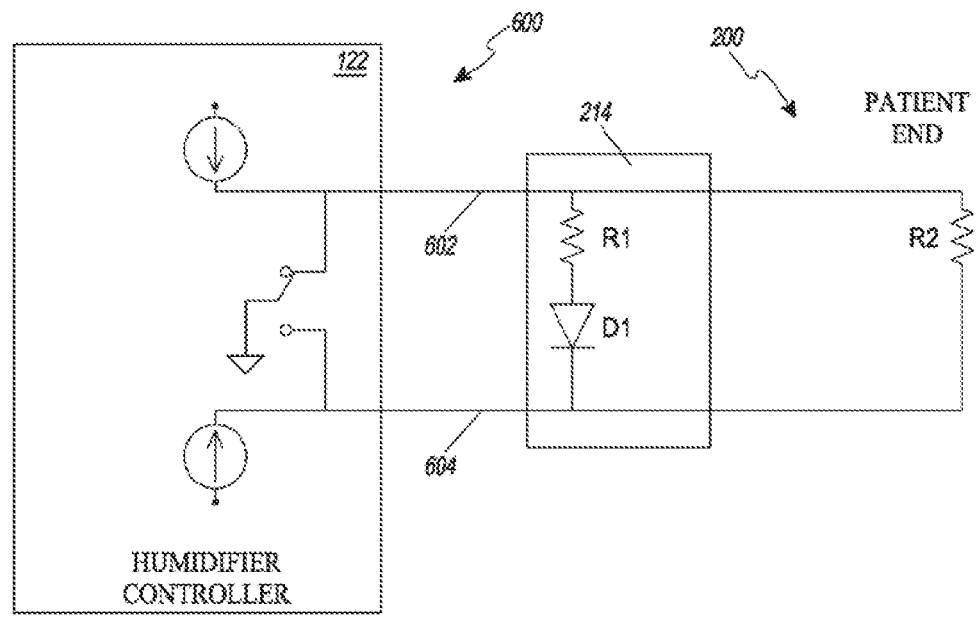
FIGS. 2L and 2M illustrate example circuit diagrams in a humidification system, wherein the circuits are configured to read data from two sensors.
Figure 2M:
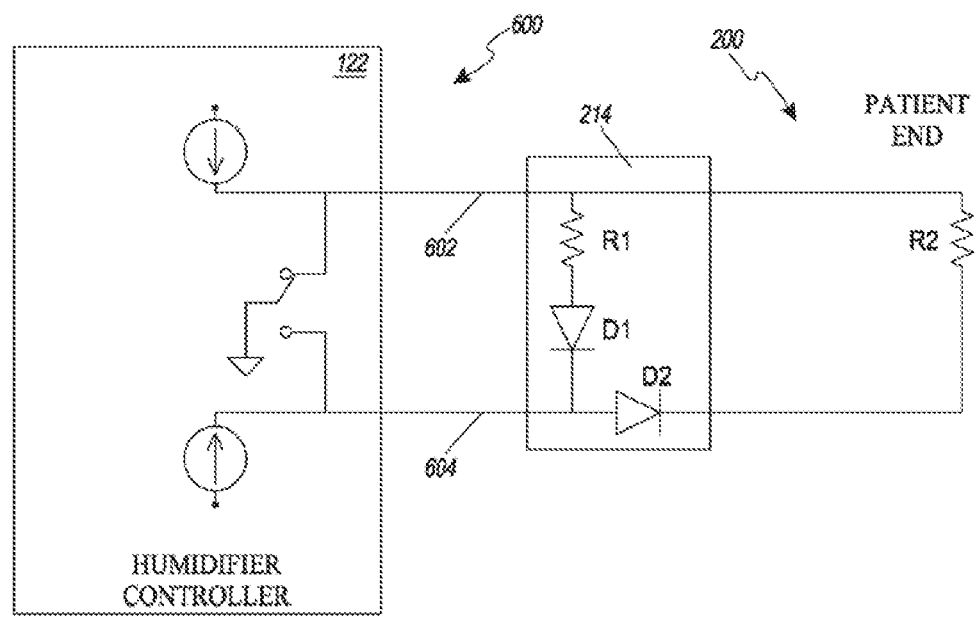

FIGS. 2L and 2M illustrate example circuit diagrams in a respiratory humidification system 100, wherein the circuit 600 is configured to read data from two sensors R1 and R2. With reference to FIGS. 2L and 2M, the sensors R1 and R2 are represented using resistors, but any suitable type of sensor can be used such as, for example and without limitation, temperature sensors, humidity sensors, flow sensors, oxygen sensors, and the like. In some embodiments, the sensors can be temperature sensors such as thermistors. In such embodiments, the sensors R1 and R2 respectively represent a first thermistor at the intermediate connector 214 and a second thermistor at a patient-end of the breathing circuit 200 (e.g., on a patient-end connector). The two thermistors R1 and R2 can be measured using two wires in the breathing circuit 200 using the circuit 600 in conjunction with a current or voltage source and switches in the humidifier controller 122. While the description with reference to FIGS. 2L and 2M involves thermistors, it is applicable to other suitable sensors which affect voltages and/or currents provided to circuits with which they are associated.

To selectively read the sensors R1 and R2, current is supplied in either polarity through lines 602 and 604. To measure the patient-end sensor R2, the humidifier controller 122 sets the switch to connect the top current supply to ground. Current then flows from the bottom current supply through R2 and to ground through the switch. Current is blocked from going through R1 by diode D1. The humidifier controller 122 can be configured to measure the voltage drop from the bottom current supply to ground, and to derive the resistance of sensor R2 based at least in part on the supplied current and measured voltage. To measure the sensor R1 positioned at the intermediate connector 214, the humidifier controller 122 can read the patient-end sensor R2 and record the result. The humidifier controller 122 can then set the switch to connect the bottom current supply to ground. Current then flows from the top current supply through R1 and R2 to ground through the switch. The humidifier controller 122 can be configured to measure the voltage drop from the top current supply to ground, and to derive the resistance of sensor R1 based at least in part on the supplied current, the measured voltage, and the recorded result from measuring the resistance of R2. In some embodiments, a voltage drop across D1 is accounted for in the derivation of the resistance of R1. In the embodiment illustrated in FIG. 2L, by placing D1 near R1, the temperature of the diode D1 can be calculated which can be used in the calculation of the voltage drop across D1. One potential advantage of the configuration illustrated in FIG. 2L is that the measurements of the sensor R2 at the patient end may be more accurate because the measurements are made without passing through a diode, as illustrated in the embodiment of FIG. 2M, which can introduce uncertainties or errors.

In some embodiments, as illustrated in FIG. 2M, an additional diode D2 can be added to the intermediate connector 214. In such embodiments, the humidifier controller 122 can be configured to measure sensors R1 and R2 in a fashion similar to the embodiment illustrated in FIG. 2L and described above. A difference is that when measuring sensor R1, current flows through R1 and D1 and not through R2 because the diode D2 blocks current flow through R2. In this way, the measurement of sensor R1 can be substantially isolated or separated from the measurement of sensor R2. Similar to the derivation of the resistance of sensor R1, the voltage drop across the diode D2 can be accounted for in deriving the resistance of sensor R2. By placing D1 and D2 near R1, the temperature of the diodes can be calculated which can be used in the calculation of the voltage drops across D1 and D2, respectively.

In certain embodiments, the measurement of sensors R1, R2 is performed in software running in a controller connected to the circuits of FIGS. 2L and 2M. The direction and amount of current supplied to the circuit can be controlled by such software. An accurate measurement of the resistance of sensors R1, R2 can be obtained by measuring the voltages using, for example, an analog to digital converter. To minimize or eliminate the effects of variances caused by the diodes D1 and/or D2, the software can supply two different currents (I1 and I2) in the same direction. This will result in two different voltage readings (V1 and V2) corresponding to the two different currents (I1 and I2). Using these two voltages and currents, the software can solve for the voltage drop of the diodes D1, D2 and resistances for sensors R1, R2, For sensor R1, for example, the voltage drop can be solved with the following equation: $Vdrop=((V1*I2-V2*I1)/((V1-V2)/R2+I2-I1))$. The resistance of sensor R1 can be calculated using the following equation: $R1=(V2-Vdrop)/(I2-V2/R2)$. In an embodiment, the calculated Vdrop has a constant error from a measured Vdrop that is corrected in software. In an embodiment, the Vdrop is increased by approximately 15% as an error compensation.

Segmented Medical Tubing for Use with Respiratory Humidification Systems

Figure 3A:
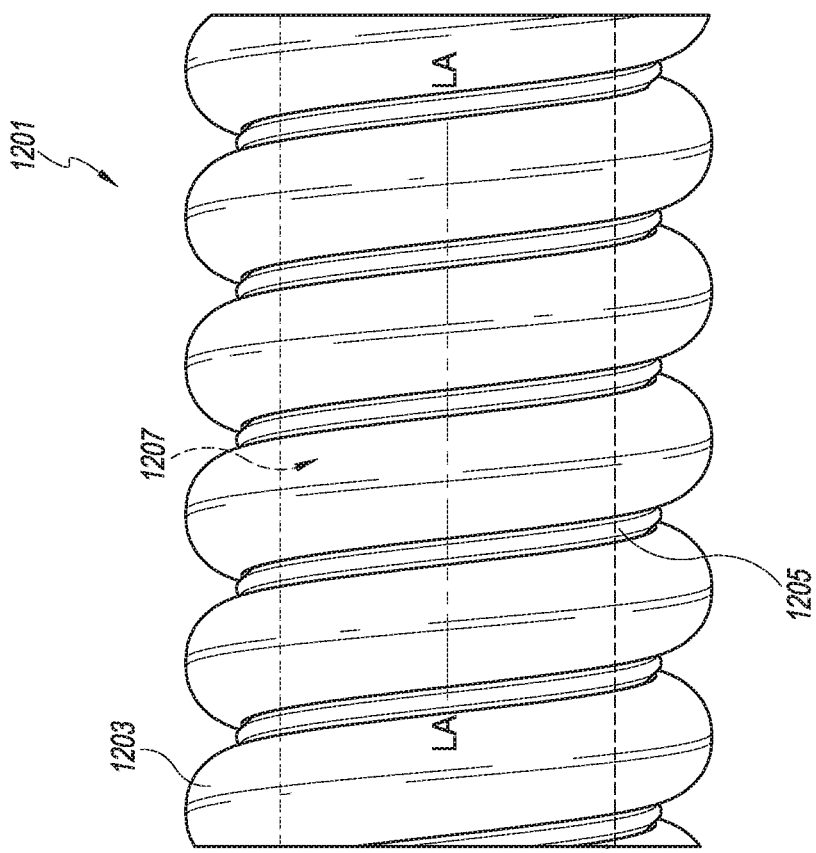
FIG. 3A shows a side-plan view of a section of an example composite tube.

FIG. 3A shows a side-plan view of a section of example composite tube 1201 which can be used in conjunction with the respiratory humidification system 100 described with reference to FIG. 1. The composite tube 1201 can be used as the inspiratory limb 202 and can be configured, as described herein, to provide thermally beneficial properties that assist in the prevention of condensation of gases along the tube. The composite tube 1201 includes a plurality of elongate members wrapped and joined to form a passageway, where the plurality of elongate members can include one or more of the heater wires described herein. Based at least in part on the heater wires being embedded in the walls of the composite tube 1201, the use of the composite tube 1201 as the inspiratory limb 202 can reduce condensation and rain out and maintain a more desirable or targeted temperature profile along the length of the inspiratory limb 202. The composite tube's walls can provide a greater thermal mass which resists temperature changes and increases the insulating effects of the walls in relation to the ambient temperature outside the limb 202. As a result, the temperature along the length of the limb 202, including through any number of differing temperature environments, can be more accurately controlled and less power or energy can be expended in controlling the temperature of the gases delivered to the patient. In some embodiments, the composite tube 1201 can be used as the expiratory limb 210.

In general, the composite tube 1201 comprises a first elongate member 1203 and a second elongate member 1205. Member is a broad term and is to be given its ordinary and customary meaning to a person of ordinary skill in the art (i.e., it is not to be limited to a special or customized meaning) and includes, without limitation, integral portions, integral components, and distinct components. Thus, although FIG. 3A illustrates an embodiment made of two distinct components, it will be appreciated that in other embodiments, the first elongate member 1203 and second elongate member 1205 can also represent regions in a tube formed from a single material. Thus, the first elongate member 1203 can represent a hollow portion of a tube, while the second elongate member 1205 represents a structural supporting or reinforcement portion of the tube which adds structural support to the hollow portion. The hollow portion and the structural supporting portion can have a spiral configuration, as described herein. The composite tube 1201 may be used to form the inspiratory limb 202 and/or the expiratory limb 210 as described herein, a coaxial tube as described below, or any other tubes as described elsewhere in this disclosure.

In this example, the first elongate member 1203 comprises a hollow body spirally wound to form, at least in part, an elongate tube having a longitudinal axis LA-LA and a lumen 1207 extending along the longitudinal axis LA-LA. In at least one embodiment, the first elongate member 1203 is a tube. Preferably, the first elongate member 1203 is flexible. Furthermore, the first elongate member 1203 is preferably transparent or, at least, semi-transparent or semi-opaque. A degree of optical transparency allows a caregiver or user to inspect the lumen 1207 for blockage or contaminants or to confirm the presence of moisture. A variety of plastics, including medical grade plastics, are suitable for the body of the first elongate member 1203. Examples of suitable materials include Polyolefin elastomers, Polyether block amides, Thermoplastic co-polyester elastomers, EPDM-Polypropylene mixtures, and Thermoplastic polyurethanes.

The hollow body structure of the first elongate member 1203 contributes to the insulating properties to the composite tube 1201. An insulating tube 1201 is desirable because, as explained herein, it prevents or reduces heat loss. This can allow the tube 1201 to deliver gas from a heater-humidifier to a patient while substantially maintaining the gas's conditioned state with reduced or minimal energy consumption.

The hollow body structure of the first elongate member can use air as an insulator. The walls of the composite tube can provide a greater thermal mass which resists temperature changes and increases the insulating effects of the walls in relation to the ambient temperature outside the tube. As a result, the temperature along the length of the tube, including through any number of differing temperature environments, can be more accurately controlled and less power or energy can be expended in controlling the temperature of the gases delivered to the patient. Further the hollow body structure also insulates or goes some way to insulate the gases inside the tube from environmental conditions and changing environmental conditions. The tube can be exposed to different conditions in different parts of the hospital (e.g., in different wards, but also could be exposed to incubators or fans or blankets positioned over parts of the tube). The hollow body structure acts to insulate the gases from such environmental changes. Further environmental changes can be changes in temperature and humidity that can occur in various regions such as for example in tropical regions.

In at least one embodiment, the hollow portion of the first elongate member 1203 is filled with a gas. The gas can be air, which is desirable because of its low thermal conductivity ($2.62\times10^{-2}$ W/m·K at 300 K) and very low cost. A gas that is more viscous than air may also advantageously be used, as higher viscosity reduces convective heat transfer. Thus, gases such as argon ($17.72\times10^{-3}$ W/m·K at 300 K), krypton ($9.43\times10^{-3}$ W/m·K at 300 K), and xenon ($5.65\times10^{-3}$ W/m·K at 300K) can increase insulating performance. Each of these gases is non-toxic, chemically inert, fire-inhibiting, and commercially available. The hollow portion of the first elongated member 1203 can be sealed at both ends of the tube, causing the gas within to be substantially stagnant. Alternatively, the hollow portion can be a secondary pneumatic connection, such as a pressure sample line for conveying pressure feedback from the patient-end of the tube to a controller. The first elongate member 1203 can be optionally perforated. For instance, the surface of the first elongate member 1203 can be perforated on an outward-facing surface, opposite the lumen 1207. In another embodiment, the hollow portion of the first elongate member 1203 is filled with a liquid. Examples of liquids can include water or other biocompatible liquids with a high thermal capacity. For instance, nanofluids can be used. An example nanofluid with suitable thermal capacity comprises water and nanoparticles of substances such as aluminum.

The second elongate member 1205 is also spirally wound and joined to the first elongate member 1203 between adjacent turns of the first elongate member 1203. The second elongate member 1205 forms at least a portion of the lumen 1207 of the elongate tube. The second elongate member 1205 acts as structural support for the first elongate member 1203.

In at least one embodiment, the second elongate member 1205 is wider at the base (proximal the lumen 1207) and narrower at the top. For example, the second elongate member can be generally triangular in shape, generally T-shaped, or generally Y-shaped. However, any shape that meets the contours of the corresponding first elongate member 1203 is suitable. Alternatively, the shape of the second elongate member may be selected to improve or reduce flexibility of a given segment. For instance, the shape may be square, rectangular, trapezoidal, diamond or parallelogram, pentagonal, or otherwise polyagonal, or the shape may be a rounded version of such shapes with radiused corners.

Preferably, the second elongate member 1205 is flexible, to facilitate bending of the tube. The second elongate member 1205 can be less flexible than the first elongate member 1203. This improves the ability of the second elongate member 1205 to structurally support the first elongate member 1203. For example, the modulus of the second elongate member 1205 is preferably 30-50 MPa (or about 30-50 MPa). The modulus of the first elongate member 1203 is less than the modulus of the second elongate member 1205. The second elongate member 1205 can be solid or mostly solid. In addition, the second elongate member 1205 can encapsulate or house conductive material, such as filaments, and specifically heating filaments or sensors (not shown). Heating filaments can minimize the cold surfaces onto which condensate from moisture-laden air can form. Heating filaments can also be used to alter the temperature profile of gases in the lumen 1207 of composite tube 1201. A variety of polymers and plastics, including medical grade plastics, are suitable for the body of the second elongate member 1205. Examples of suitable materials include Polyolefin elastomers, Polyether block amides, Thermoplastic co-polyester elastomers, EPDM-Polypropylene mixtures and Thermoplastic polyurethanes. In certain embodiments, the first elongate member 1203 and the second elongate member 1205 may be made from the same material. The second elongate member 1205 may also be made of a different color material from the first elongate member 1203, and may be transparent, translucent or opaque. For example, in one embodiment the first elongate member 1203 may be made from a clear plastic, and the second elongate member 1205 may be made from an opaque blue (or other color) plastic.

This spirally-wound structure comprising a flexible, hollow body and an integral support can provide crush resistance, while leaving the tube wall flexible enough to permit short-radius bends without kinking, occluding or collapsing. Preferably, the tube can be bent around a 25 mm diameter metal cylinder without kinking, occluding, or collapsing, as defined in the test for increase in flow resistance with bending according to ISO 5367:2000(E). This structure also can provide a smooth lumen 1207 surface (tube bore), which helps keep the tube free from deposits and improves gas flow. The hollow body has been found to improve the insulating properties of a tube, while allowing the tube to remain light weight.

As explained above, the composite tube 1201 can be used as an expiratory tube and/or an inspiratory tube in a breathing circuit, or a portion of a breathing circuit. Preferably, the composite tube 1201 is used at least as an inspiratory tube.

Figure 3B:
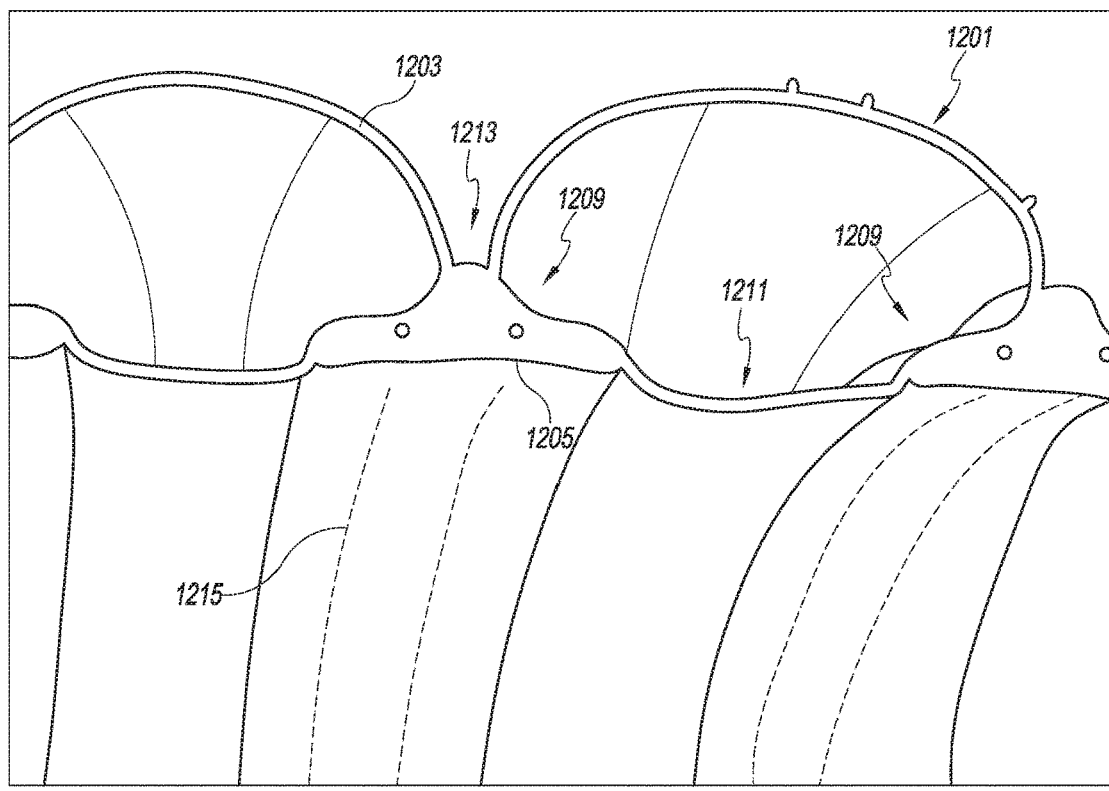
FIG. 3B shows a longitudinal cross-section of a top portion a tube similar to the example composite tube of FIG. 3A.

FIG. 3B shows a longitudinal cross-section of a top portion of the example composite tube 1201 of FIG. 3A. FIG. 3B has the same orientation as FIG. 3A. This example further illustrates the hollow-body shape of the first elongate member 1203. As seen in this example, the first elongate member 1203 forms in longitudinal cross-section a plurality of hollow bubbles, which are fully enclosed within the composite tube. The hollow bubbles can be filled with air. Portions 1209 of the first elongate member 1203 overlap adjacent wraps of the second elongate member 1205. A portion 1211 of the first elongate member 1203 forms the wall of the lumen (tube bore).

It was discovered that having a gap 1213 between adjacent turns of the first elongate member 1203, that is, between adjacent bubbles, unexpectedly improved the overall insulating properties of the composite tube 1201. Thus, in certain embodiments, adjacent bubbles are separated by a gap 1213. Furthermore, certain embodiments include the realization that providing a gap 1213 between adjacent bubbles increases the heat transfer resistivity (the R value) and, accordingly, decreases the heat transfer conductivity of the composite tube 1201. This gap configuration was also found to improve the flexibility of the composite tube 1201 by permitting shorter-radius bends. A T-shaped second elongate member 1205, as shown in FIG. 3B, can help maintain a gap 1213 between adjacent bubbles. Nevertheless, in certain embodiments, adjacent bubbles are touching. For example, adjacent bubbles can be bonded together.

One or more conductive materials can be disposed in the second elongate member 1205 for heating or sensing the gas flow. In this example, two heating filaments 1215 are encapsulated in the second elongate member 1205, one on either side of the vertical portion of the "T." The heating filaments, also referred to as heater wires, 1215 comprise conductive material, such as alloys of Aluminum (Al) and/or Copper (Cu), or conductive polymer. Preferably, the material forming the second elongate member 1205 is selected to be non-reactive with the metal in the heating filaments 1215 when the heating filaments 1215 reach their operating temperature. The filaments 1215 may be spaced away from lumen 1207 so that the filaments are not exposed to the lumen 1207. At one end of the composite tube, pairs of filaments can be formed into a connecting loop.

In at least one embodiment, a plurality of filaments are disposed in the second elongate member 1205. The filaments can be electrically connected together to share a common rail. For example, a first filament, such as a heating filament, can be disposed on a first side of the second elongate member 1205. A second filament, such as a sensing filament, can be disposed on a second side of the second elongate member 1205. A third filament, such as a ground filament, can be disposed between the first and second filaments. The first, second, and/or third filaments can be connected together at one end of the second elongate member 1205.

Figure 3C:
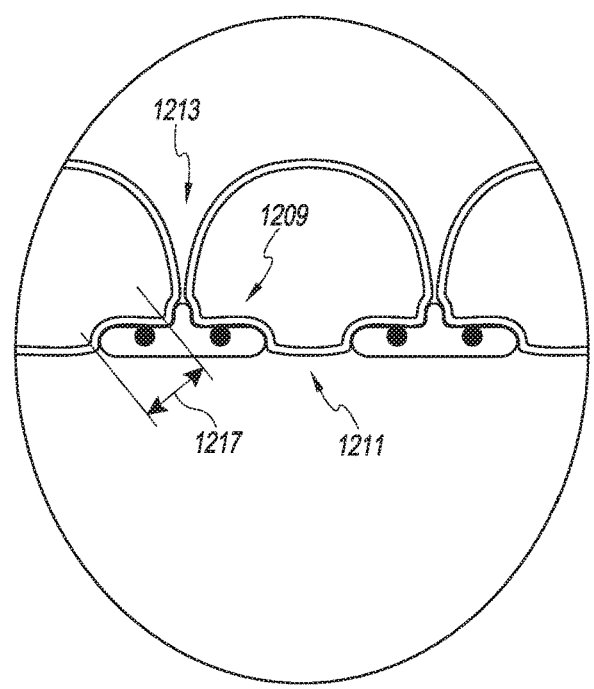
FIG. 3C shows another longitudinal cross-section illustrating a first elongate member in the composite tube.
Figure 3D:
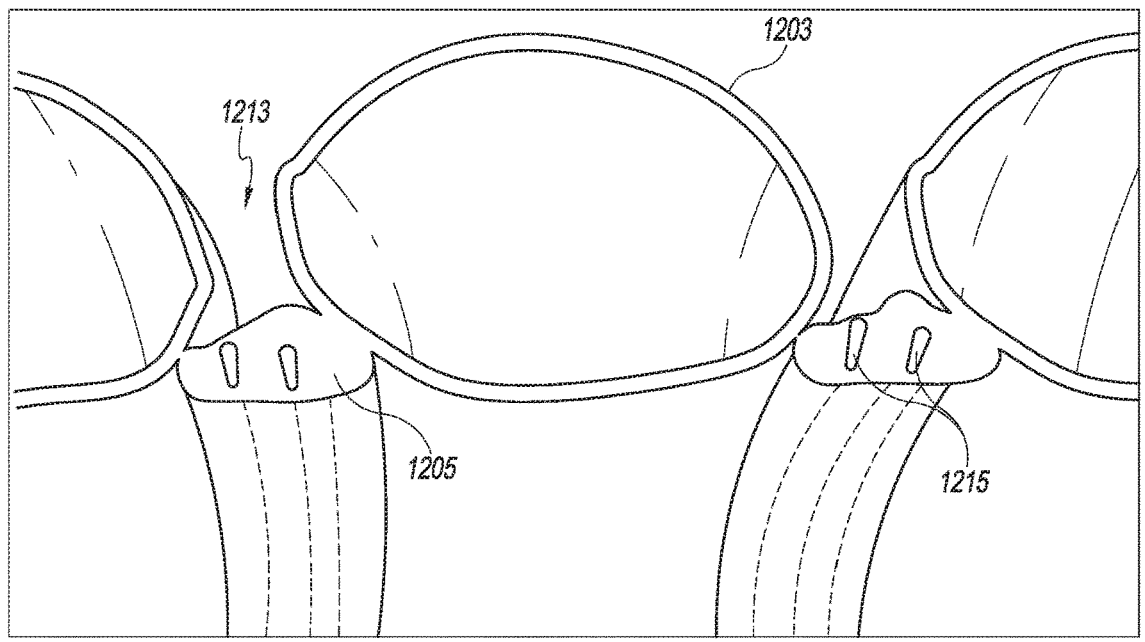
FIG. 3D shows another longitudinal cross-section of a top portion of a tube.

FIG. 3C shows a longitudinal cross-section of the bubbles in FIG. 3B. As shown, the portions 1209 of the first elongate member 1203 overlapping adjacent wraps of the second elongate member 1205 are characterized by a degree of bond region 1217. A larger bond region improves the tubes resistance to delamination at the interface of the first and second elongate members. Additionally or alternatively, the shape of the bead and/or the bubble can be adapted to increase the bond region 1217. For example, FIG. 3D shows a relatively small bonding area on the left-hand side. FIG. 4B also demonstrates a smaller bonding region. In contrast, FIG. 3E has a much larger bonding region than that shown in FIG. 3D, because of the size and shape of the bead. FIGS. 4A and 4C also illustrate a larger bonding region. Each of these figures is discussed in more detail below. It should be appreciated that although the configurations in FIGS. 3E, 4A, and 4C may be preferred in certain embodiments, other configurations, including those of FIGS. 3D, 4B, and other variations, may be utilized in other embodiments as may be desired.

FIG. 3D shows a longitudinal cross-section of a top portion of another composite tube. FIG. 3D has the same orientation as FIG. 3B. This example further illustrates the hollow-body shape of the first elongate member 1203 and demonstrates how the first elongate member 1203 forms in longitudinal cross-section a plurality of hollow bubbles. In this example, the bubbles are completely separated from each other by a gap 1213. A generally triangular second elongate member 1205 supports the first elongate member 1203.

Figure 3E:
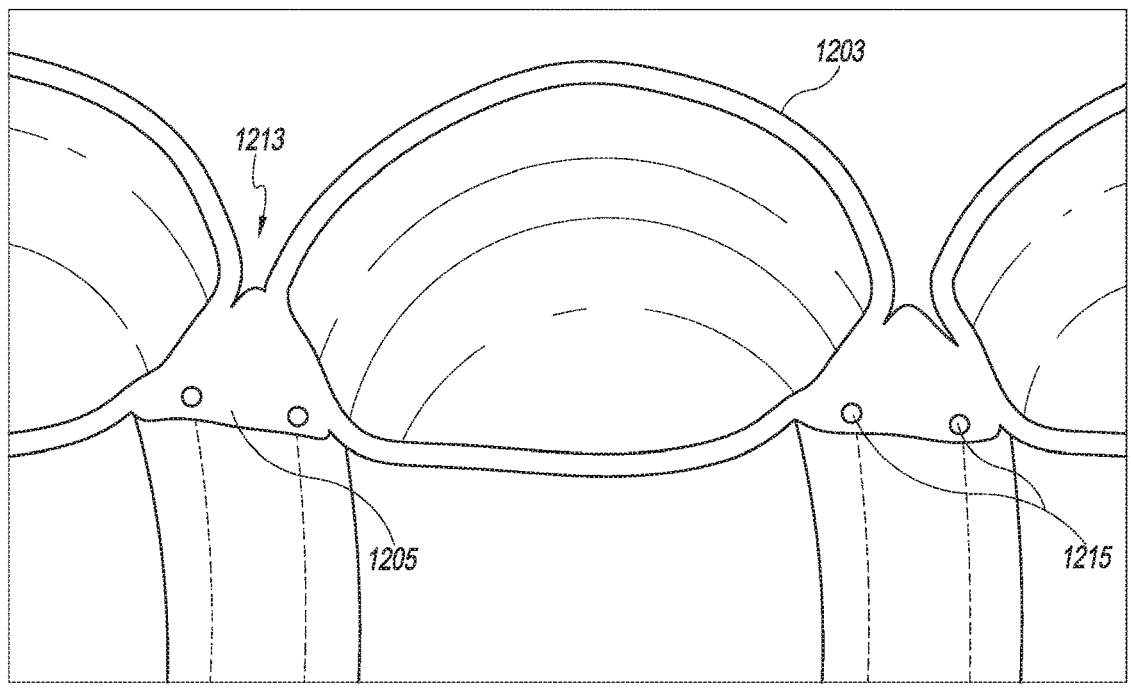
FIG. 3E shows another longitudinal cross-section of a top portion of a tube.
Figure 4A:
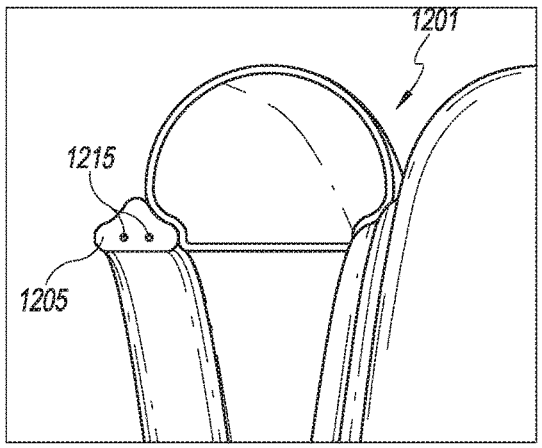
FIGS. 4A-C show examples of first elongate member shapes configured to improve thermal efficiency.
Figure 4B:
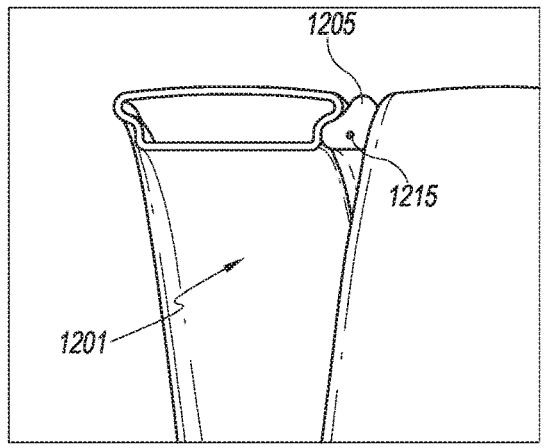
Figure 4C:
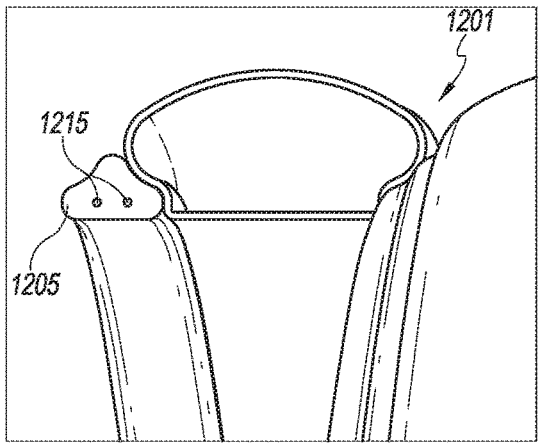
Figure 4D:
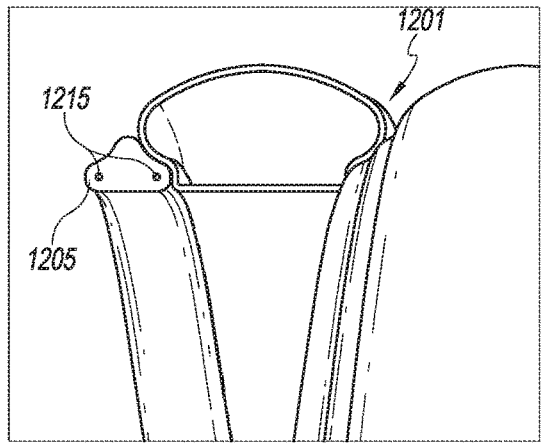
FIGS. 4D-F show examples of filament arrangements configured to improve thermal efficiency.
Figure 4E:
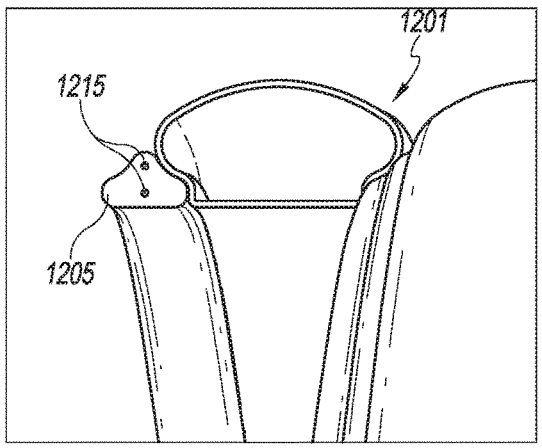
Figure 4F:
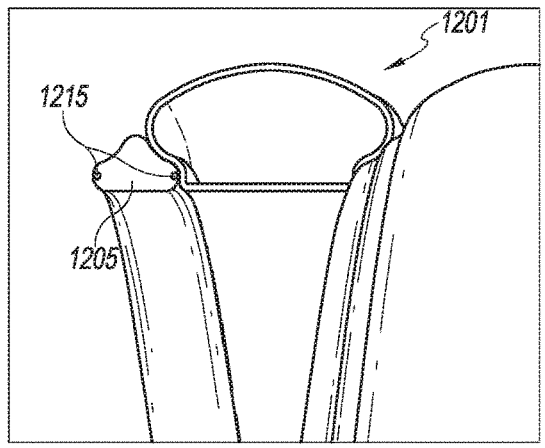

FIG. 3E shows a longitudinal cross-section of a top portion of another composite tube. FIG. 3E has the same orientation as FIG. 3B. In the example of FIG. 3E, the heating filaments 1215 are spaced farther apart from each other than the filaments 1215 in FIG. 3B. It was discovered that increasing the space between heating filaments can improve heating efficiency, and certain embodiments include this realization. Heating efficiency refers to the ratio of the amount of heat input to the tube to the amount of energy output or recoverable from the tube. Generally speaking, the greater the energy (or heat) that is dissipated from the tube, the lower the heating efficiency. For improved heating performance, the heating filaments 1215 can be equally (or about equally) spaced along the bore of the tube. Alternatively, the filaments 1215 can be positioned at extremities of the second elongate member 1205, which may provide simpler manufacturing.

FIG. 4A shows a longitudinal cross-section of a top portion of a composite tube. FIG. 4A shows an embodiment of a composite tube 1201 where the first elongate member, (i.e., the bubble), has a large height. In this example, the bubble has a relatively small radius of curvature and therefore a large curvature. Also, the bubble is approximately three to four times greater in height than the height of the second elongate member 1205.

FIG. 4B shows a longitudinal cross-section of a top portion of another composite tube. FIG. 4B shows an embodiment of a composite tube 1201 where the first elongate member (i.e., the bubble) is flattened on top. In this example, the bubble has a very large radius of curvature but a small curvature. Also, the bubble is approximately the same height as the second elongate member 1205.

FIG. 4C shows a longitudinal cross-section of a top portion of another composite tube. FIG. 4C shows an embodiment of a composite tube 1201 where the width of the first elongate member (i.e., the bubble) is greater than the height of the first elongate member (i.e., the bubble). In this example, the bubble has radius of curvature and the curvature between that of FIG. 4A and FIG. 4B, and the center of the radius for the upper portion of the bubble is outside of the bubble (as compared to FIG. 4A). The inflection points on the left and right sides of the bubble are about at the middle (heightwise) of the bubble (as opposed to in the lower portion of the bubble, as in FIG. 4A). Also, the height of the bubble is approximately double that of the second elongate member 1205, resulting in a bubble height between that of FIG. 4A and FIG. 4B.

The configuration of FIG. 4A resulted in the lowest heat loss from the tube. The configuration of FIG. 4B resulted in the highest heat loss from the tube. The configuration of FIG. 4C had intermediate heat loss between the configurations of FIGS. 4A and 4B. However, the large external surface area and convective heat transfer in the configuration of FIG. 4A led to inefficient heating. Thus, of the three first elongate member (i.e., the bubble) arrangements of FIGS. 4A-4C, FIG. 4C was determined to have the best overall thermal properties. When the same thermal energy was input to the three tubes, the configuration of FIG. 4C allowed for the largest temperature rise along the length of the tube. The bubble of FIG. 4C is sufficiently large to increase the insulating air volume, but not large enough to cause a significant convective heat loss. The configuration of FIG. 4B was determined to have the poorest thermal properties, namely that the configuration of FIG. 4B allowed for the smallest temperature rise along the length of the tube. The configuration of FIG. 4A had intermediate thermal properties and allowed for a lower temperature rise than the configuration of FIG. 4C.

It should be appreciated that although the FIG. 4C configuration may be preferred in certain embodiments, other configurations, including those of FIGS. 4A, 4B and other variations, may be utilized in other embodiments as may be desired.

TABLE 1 shows the height of the first elongate member (i.e., the bubble), the outer diameter of the tube, and the radius of curvature of the configurations shown in each of FIGS. 4A, 4B, and 4C.

TABLE 1

|  | Tube (FIG.) | | |
| --- | --- | --- | --- |
|  | 4A | 4B | 4C |
| Bubble height (mm) | 3.5 | 5.25 | 1.75 |
| Outer diameter (mm) | 21.5 | 23.25 | 19.75 |
| Radius of curvature (mm) | 5.4 | 3.3 | 24.3 |

Tube Flexibility

FIGS. 5A-5E provide examples of modifications to the first elongate member and second elongate member that can alter the flexibility of a composite tube 1201. The geometry of the tube 1201 also affects the mechanical properties of the tube. By altering flexibility and rigidity, the mechanical properties of the tube 1201 can be customized. It should be appreciated that each of the modifications discussed below has its stated effects in isolation (i.e., if all else is kept the same). However, it should be appreciated that one of skill in the art could use one or more than one of the modifications described below to achieve the desired tube with appropriate the appropriate lumen bore, outer diameter, outer profile, aesthetic appearance, flexibility/rigidity, length, insulation characteristics, or other desired features. Flexibility of the tube may refer to defined standards, such as industry standards, for bending without kinking, occluding, or having too high of an increased resistance to flow within the tube. By increasing the flexibility, the present disclosure contemplates tubes that can be more flexible than the defined standard. A tube having increased flexibility can indicate that the tube can bend at a smaller radius of curvature and/or with less force required to make a bend in the tube.

Diameter

Figure 5A:
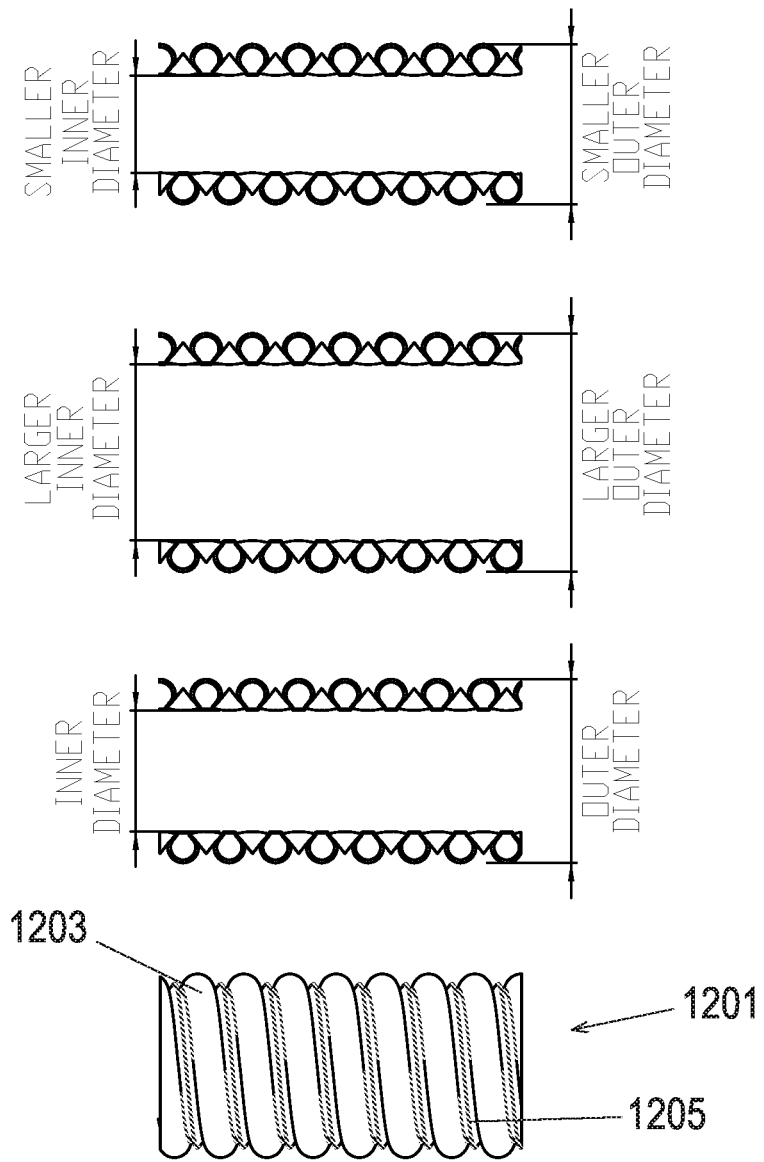
FIGS. 5A-E show examples of first elongate member and second elongate member shapes configured to improve flexibility.

FIG. 5A illustrates alterations to the diameter of the lumen and the size of the diameter of the first elongate member. By increasing the size of the bubble of the first elongate member, the flexibility of the tube 1201 will increase. Conversely, a smaller bubble size will produce a more rigid region of the tube 1201. For example, the diameter of the first elongate member can be in the range of 1.0 mm (or about 1.0 mm) and 6.0 mm (or about 6.0 mm).

By increasing the inner diameter of the tube, the flexibility of the tube 1201 will decrease. Conversely, a smaller tube inner diameter will increase the flexibility of the tube 1201. For example, the inner diameter of the tube can be in the range of 6.0 mm (or about 6.0 mm) and 30.0 mm (or about 30.0 mm). By varying the inner diameter of the tube 1201, it is possible to have a smaller inner diameter near a patient interface which can increase patient comfort, improve the aesthetics, and reduce the invasiveness of the interface.

Wall Thickness

Figure 5B:
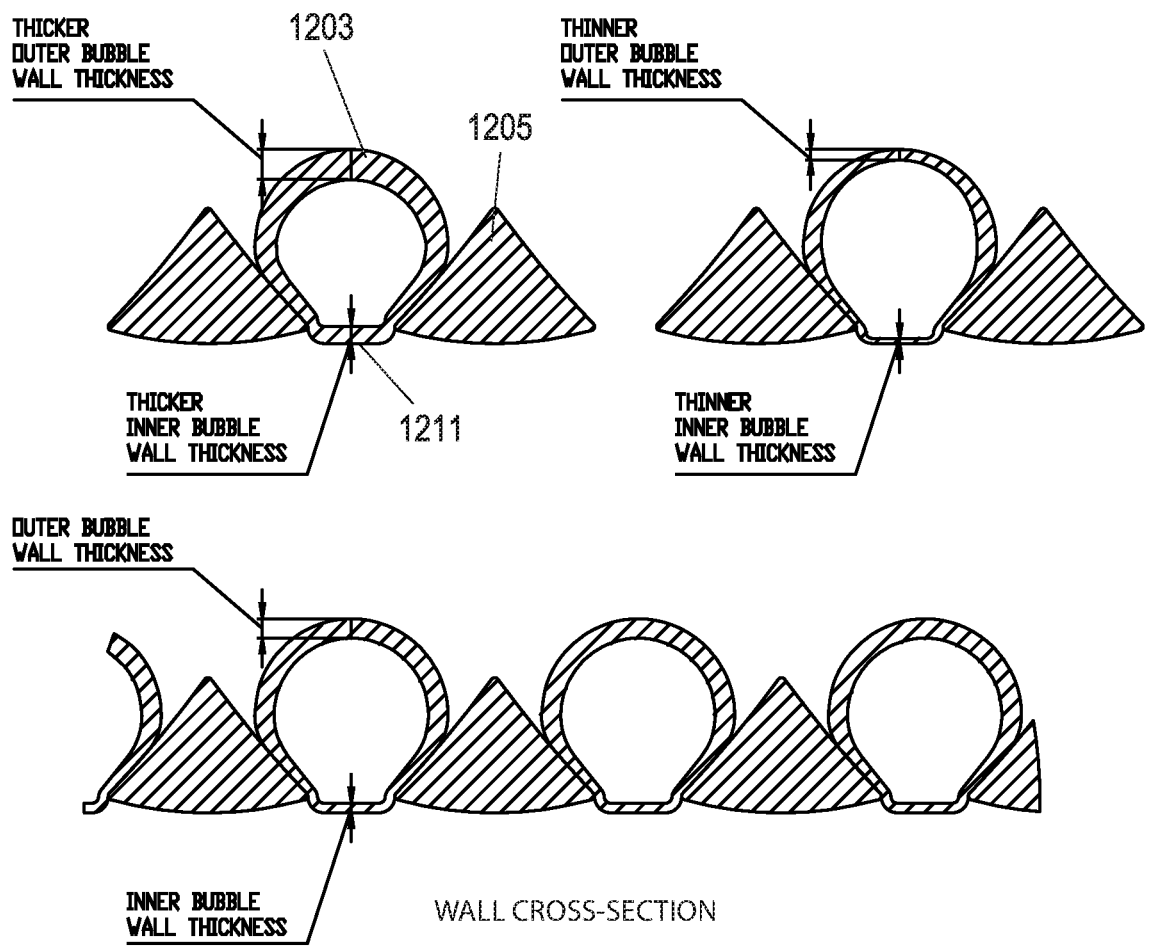
Figure 5B:
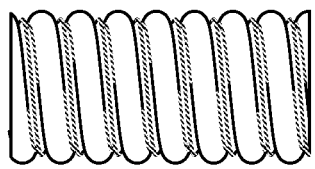

In the example of FIG. 5B, the cross-sectional thickness of the inner portion 1211 of the first elongate member 1203 forming the wall of the lumen is less than the thickness of the outer portion. Because the configuration of FIG. 5B results in a thinner bubble near the lumen, such a configuration allows the inner portion 1211 to compress or "bunch" more readily when the composite tube 1201 is bent into a ∩-shape. Thus, certain embodiments include the realization that a configuration in which the cross-sectional thickness of the inner portion 1211 is less than the cross-sectional thickness of the outer portion can improve the flexibility of the composite tube 1201 by permitting shorter radius bends. In addition, certain embodiments include the realization that overall tube flexibility can be improved by providing a first elongate member 1203 with a variable cross-sectional wall thickness. Desirably, the thickness of the inner portion 1211 is less than the thickness of the outer portion.

In at least one embodiment, the thickness of the inner portion 1211 is at least 20% (or about 20%) less than the thickness of the outer portion. For example, in certain embodiments, the thickness of the inner portion 1211 is at least 30% (or about 30%), at least 40% (or about 40%), at least 50% (or about 50%), or at least 60% (or about 60%) less than the thickness of the outer portion. In certain embodiments, the thickness of the inner portion 1211 is 27% (or about 27%) less than the thickness of the outer portion. In certain embodiments, the thickness of the inner portion 1211 is 32% (or about 32%) less than the thickness of the outer portion. In certain embodiments, the thickness of the inner portion 1211 is 58% (or about 58%) less than the thickness of the outer portion. In certain embodiments, the thickness of the inner portion 1211 is 64% (or about 64%) less than the thickness of the outer portion.

The thickness of the outer portion can be in the range of 0.14 mm (or about 0.14 mm) and 0.5 mm (or about 0.5 mm), and preferably in the range of 0.20 mm (or about 0.20 mm) and 0.50 mm (or about 0.50 mm). The thickness of the inner portion 1211 can be in the range of 0.05 mm (or about 0.05 mm) and 0.30 mm (or about 0.30 mm), and preferably in the range of 0.08 mm (or about 0.08 mm) and 0.15 mm (or about 0.15 mm).

Pitch

Figure 5C:
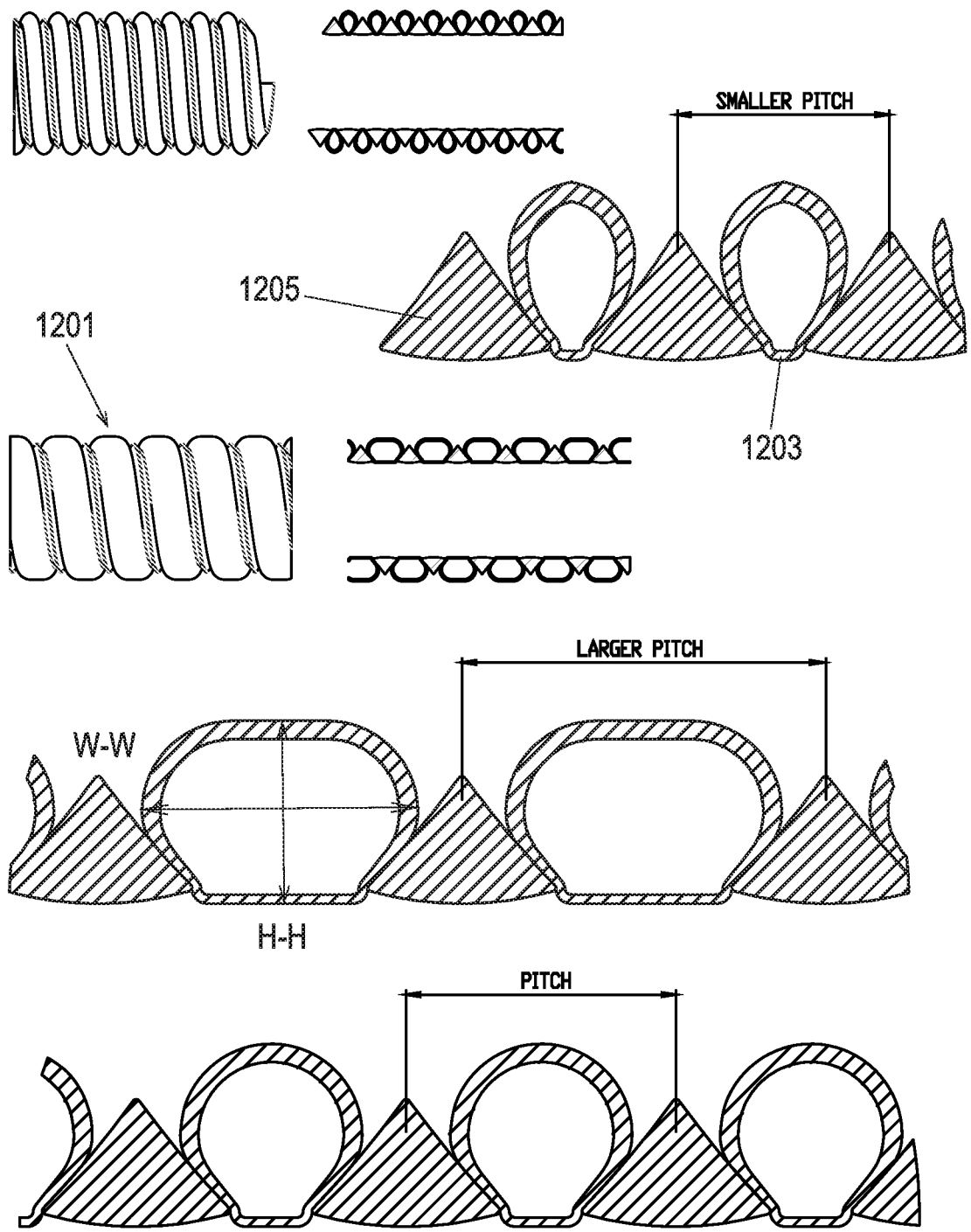

Referring to FIG. 5C, the pitch of the windings of the first elongate member 1203 can be changed to affect the flexibility of the tube. The pitch refers to the spacing of one winding of one member to the next of the same member. For example, the pitch can refer to the spacing from the first elongate member to the next first elongate member, from the second elongate member to the next second elongate member, the middle of the member to the next middle and so forth. A smaller pitch can result in the height (H-H) that is greater than the width (W-W) of a single longitudinal cross-sectional bubble of the first elongate member 1203. Because a greater height increases the amount of material slack in the outer wall of the bubble of the first elongate member 1203, such configuration can improve the flexibility of the composite tube 1201 by permitting shorter radius bends. Accordingly, certain embodiments include the realization that overall tube flexibility can be improved by reducing the pitch and providing a first elongate member 1203 with a longitudinal cross-sectional height that is greater than the longitudinal cross-sectional width. It should be appreciated that, although this example configuration may be preferred in certain embodiments, other configurations and variations, may be used in other embodiments as may be desired. For example, the height of a longitudinal cross-sectional bubble of the first elongate member 1203 can be less than its width.

However, it should be appreciated by one of skill that generally a wider pitch will provide a more flexible tube (i.e., a bubble with a relatively larger W-W). For instance, a tube with large height H-H and small width W-W will be less flexible than a tube with large width W-W. The cross-factor of large H-H and large W-W may be greater still in flexibility (than a small height H-H and large width W-W), because it is W-W also has a significant impact of flexibility.

In at least one embodiment, the bubble height (H-H) can be in the range of 1.2 mm (or about 1.2 mm) and 10 mm (or about 10 mm), such as 1.2 mm (or about 1.2 mm), 1.7 mm (or about 1.7 mm), 1.8 mm (or about 1.8 mm), 2.7 mm (or about 2.7 mm), 2.8 mm (or about 2.8 mm), 3 mm (or about 3 mm), 3.2 mm (or about 3.2 mm), 3.5 mm (or about 3.5 mm), 3.8 mm (or about 3.8 mm), 4 mm (or about 4 mm), 4.5 mm (or about 4.5 mm), 7.7 mm (or about 7.7 mm), or 8.2 mm (or about 8.2 mm), In at least one embodiment, the bubble width (W-W) can be in the range of 1.7 mm (or about 1.7 mm) and 8 mm (or about 8 mm), such as 1.7 mm (or about 1.7 mm), 3.2 mm (or about 3.2 mm), 3.5 mm (or about 3.5 mm), 4.0 mm (or about 4.0 mm), 4.2 mm (or about 4.2 mm), 5.2 mm (or about 5.2 mm), 5.5 mm (or about 5.5 mm), 6 mm (or about 6 mm), 7 mm (or about 7 mm), 7.5 mm (or about 7.5 mm), or 8 mm (or about 8 mm).

The relationship between bubble height (H-H) and bubble width (W-W) can be expressed as a ratio. A ratio of bubble height (H-H) to bubble width (W-W) equal to 0 is least flexible. Flexibility increases as the ratio increases. In at least one embodiment, the ratio of bubble height (H-H) to bubble width (W-W) can be in the range of 0.15 (or about 0.15) and 1.5 mm (or about 1.5), such as 0.16 (or about 0.16), 0.34 (or about 3.4), 0.50 (or about 0.50), 0.56 (or about 0.56), 0.57 (or about 0.57), 0.58 (or about 0.58), 0.67 (or about 0.67), 0.68 (or about 0.68), 0.73 (or about 0.73), 0.85 (or about 0.85), 1.1 (or about 1.1). and 1.3 (or about 1.3).

Bead Width

Figure 5D:
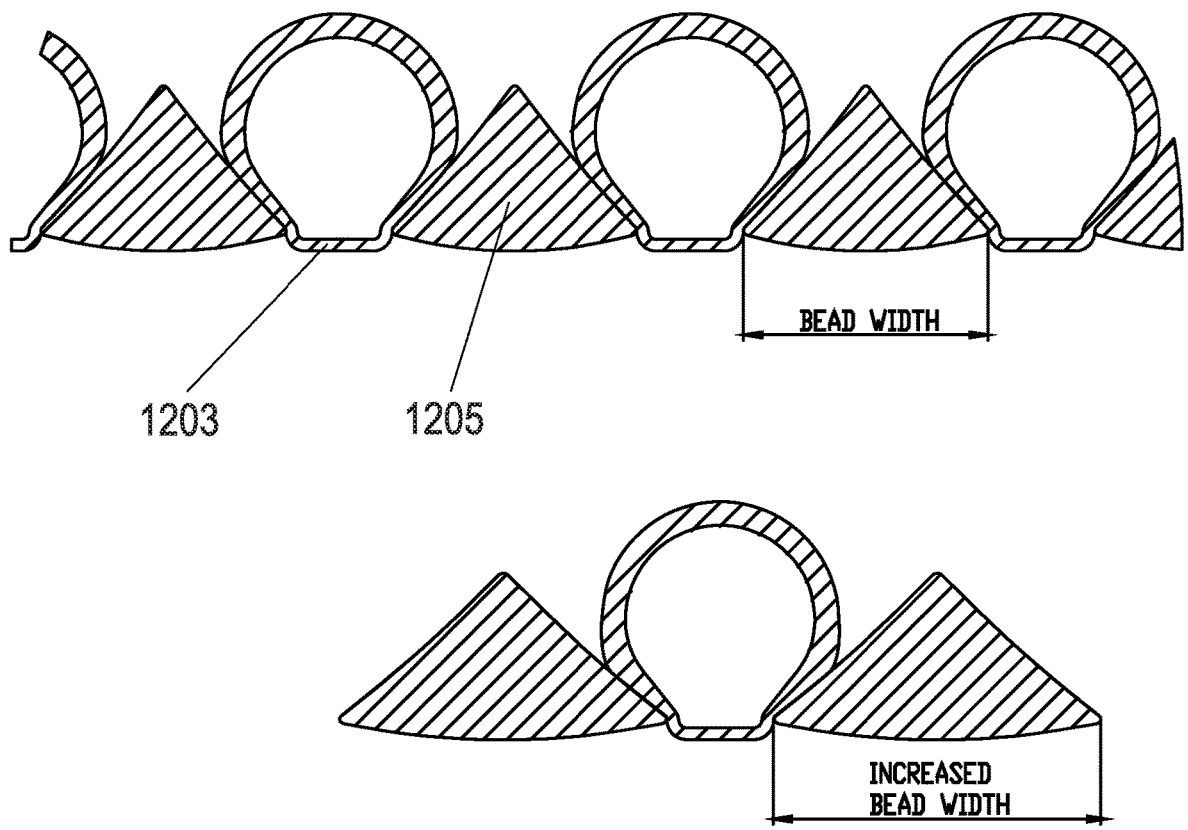

FIG. 5D illustrates alterations to the width of the second elongate member. The second elongate member 1205 can be flexible, to facilitate bending of the tube. For example, the modulus of the second elongate member 1205 is preferably 30-50 MPa (or about 30-50 MPa). The modulus of the first elongate member 1203 can be less than the modulus of the second elongate member 1205. The second elongate member 1205 can be solid or mostly solid. The width of the second elongate member 1205 can be increased to alter the flexibility of the tube. A greater width of the second elongate member 1206 with the same pitch would decrease flexibility (as it would also effectively decrease the width of the first elongate member 1203). Excessive width of the second elongate member 11205 can limit the bend radius and cause the tube to bunch or collapse. A greater width at of the second elongate member 1205 at the same pitch also reduces the free length available to bend the inner wall of the first elongate member 1203, and thus creates a stiffer tube. It can also increase the bond between the first and second elongate members reducing the slack length in the upper portion of the first elongate member.

Flat Bubble

Figure 5E:
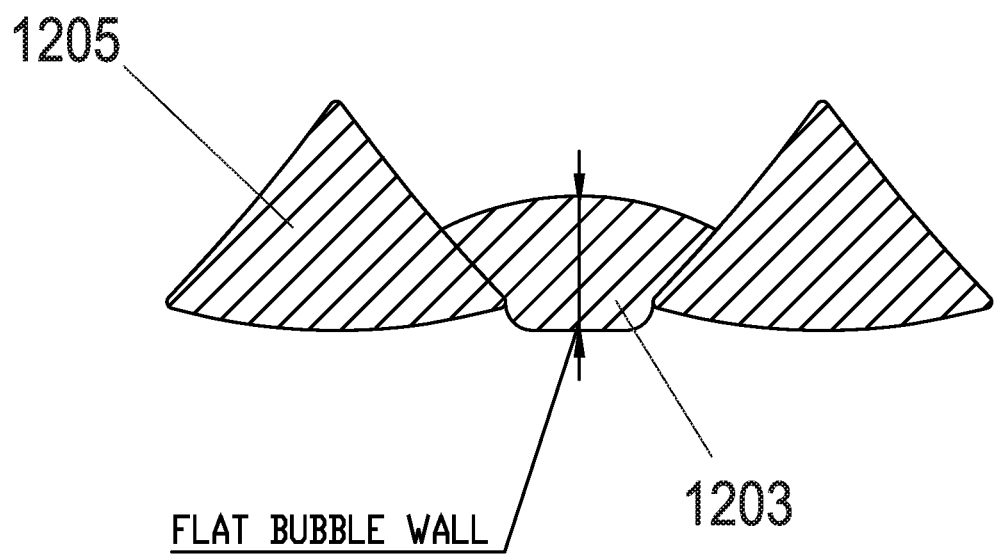

FIG. 5E illustrates an embodiment of the first elongate member where the bubble is flattened on top and solid. The flattened body of the first elongate member can decrease the flexibility of the tube. A flattened bubble section can stiffen the tube significantly. In some embodiments, the flattened bubble can be mostly solid, but can be slightly open (not shown).

Variable-Stiffness Tube

Figure 6A:
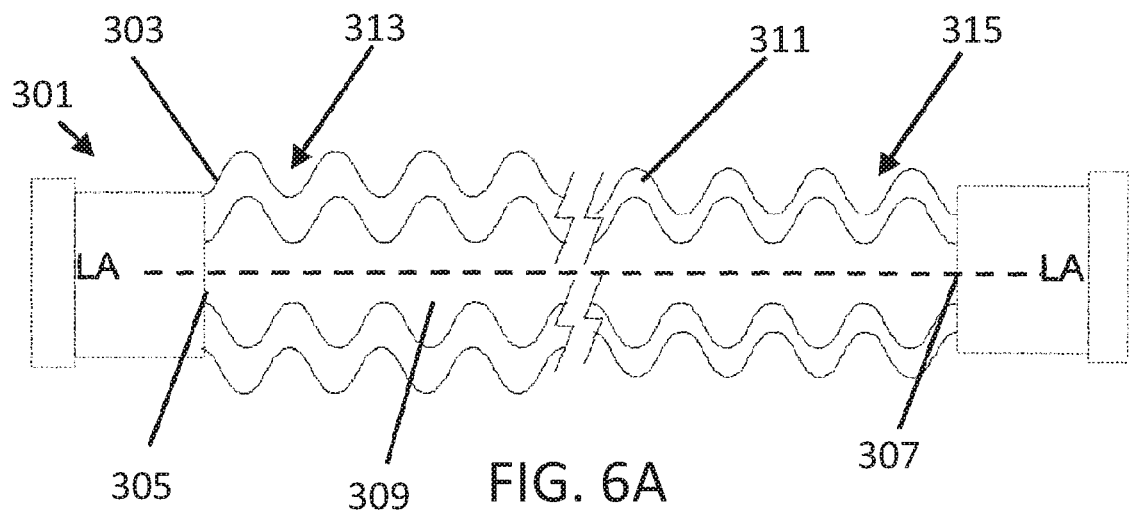
FIGS. 6A-6C show, longitudinal cross sections of example composite tubes.

FIG. 6A shows a longitudinal cross section of example variable-thickness tube 301. In general, the medical tube 301 comprises an elongate conduit 303 having a first opening 305, a second opening 307, and a longitudinal axis LA-LA. In this example, the elongate conduit 303 has a generally cylindrical shape. Nevertheless, "conduit" is a broad term and is to be given its ordinary and customary meaning to a person of ordinary skill in the art (that is, it is not to be limited to a special or customized meaning) and includes, without limitation, non-cylindrical passageways. A lumen 309 extends between the first opening 305 and the second opening 307 along the longitudinal axis LA-LA. The conduit 303 is stiffer adjacent the first opening 305 than it is adjacent the second opening 307.

The conduit 303 comprises a wall 311, extending between the first opening 305 and the second opening 307, and surrounding the lumen 309. In this example, the wall 311 is stiffer in a first region 313 of the conduit 303 adjacent the first opening 305 than in a second region 315 of the conduit 303 adjacent the second opening 307. The wall 311 can be optionally corrugated, or of a corrugate profile. As shown in this example, the corrugation profile can comprise of alternating outer crests (or annular protrusions) and inner troughs (or annular recesses). The outer crests can correspond to a location of maximum inner radius and maximum outer radius of the elongate conduit, and the inner troughs can correspond to a location of minimum inner radius and minimum outer radius of the elongate conduit. Such corrugations may be of an annular corrugation or spiral corrugation form. Alternatively, the wall 311 can be of a smooth or non-corrugated profile. Optionally, the first opening 305 is configured in size and shape to connect to a source of humidified gas, such as a humidifier described above, and the second opening 307 is configured in size and shape to connect to a patient interface. For instance, one or more ends can be configured to connect to a connection port which facilitates connection to the patient interface and/or humidifier. Other configurations can also be desirable. For example, in other embodiments, the first opening 305 can be configured to connect to a patient interface, while the second opening 307 can be configured to connect to a ventilator/blower, as described above.

As described in greater detail below, the tube 301 can optionally include one or more conductive (heating or sensing) filaments. Optional positions for the filaments are: placed within the lumen, typically in a loose, spiral fashion; placed in close external contact to the tube wall, typically in conjunction with an external sheath to secure the conductive filaments) in place and prevent heat loss; or embedded in the tube wall.

In general, the total length of the tube can be between 1.0 m and 3.0 m (or about 1.0 m and 3.0 m) or between 1.0 and 2.0 m (or about 1.0 and 2.0 m). Preferably, the length of the tube is 1.5 m (or about 1.5 m) or 1.8 in (or about 1.8 m). Preferably, the average diameter of the lumen (accounting for the variability in diameter created by the crests and troughs in optional corrugation) is between 9 mm and 30 mm (or about 9 mm and 30 mm). Preferably, the lumen diameter for an adult patient is 20 mm (or about 20 mm) or 22 mm (or about 22 mm). Preferably, the lumen diameter for a neonate patient is 9 mm (or about 9 mm) to 15 mm (or about 15 mm). In fact, it is contemplated that the variable-stiffness tubes described herein can be used as a replacement for tubes previously used in the art, which typically have an average lumen diameter between 9 mm and 30 mm and length ranging between about 1 m and 2.5 m.

It is also preferable that the tube be resistant to crushing, resistant to restrictions in flow when bent, resistant to kinking, resistant to changes in length and/or volume under internal pressure, resistant to leaking (<25 mL/min at 6 kPa), have low flow resistance (the increase in pressure at maximum rated flow is less than 0.2 kPa), and be electrically safe. Preferably, the tube can be bent around a 25 mm diameter metal cylinder without kinking, occluding, or collapsing, as defined in the test for increase in flow resistance with bending according to ISO 5367:2000(E).

Different Stiffness Between Regions

Figure 6B:
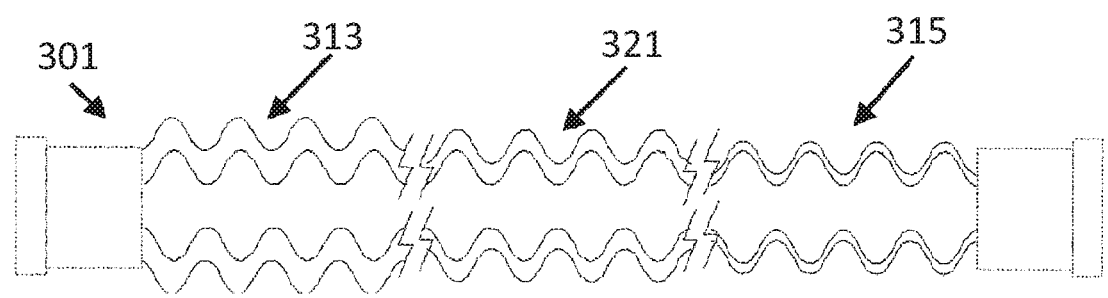

Referring again to FIG. 6A, preferably, a first region 313 of the conduit 303 adjacent the first opening 305 is stiffer than a second region 315 of the conduit 303 adjacent the second opening 307. Various embodiments include one or more additional regions between the first region 313 and the second region 315 having different stiffness characteristics than the first region 313 and the second region 315 (for example, stiffness characteristics intermediate those of the first region 313 and the second region 315). A three-region tube 301, for example, can impart a better curving profile in comparison to a two-region tube 301. A three-region tube 301 schematic is shown in FIG. 6B. This example comprises a third region 321 intermediate the first region 313 and the second region 315, Wall Composition In at least one embodiment, the wall is formed from an extrudate comprising one or more polymers. Preferred polymers include Linear Low Density Polyethylene (LLDPE), Low Density Polyethylene (LDPE), Polypropylene (PP), Polyolefin Plastomer (POP), Ethylene Vinyl Acetate (EVA), Plasticized Polyvinylchloride (PVC), or a blend of two or more of these materials. The polymer(s) forms at least 98.4 (or about 98.4), 98.5 (or about 98.5), 98.6 (or about 98.6), 98.7 (or about 98.7), 98.8 (or about 98.8), 98.9 (or about 98.9), 99.0 (or about 99.0), 99.1 (or about 99.1), 99.2 (or about 99.2), 99.3 (or about 99.), 99.4 (or about 99.4), 99.5 (or about 99.5), 99.6 (or about 99.6), 99.7 (or about 99.7), 99.8 (or about 99.8), or 99.9 (or about 99.9) weight percent (wt. %) of the total extrudate. In particular embodiments, the extrudate comprises 99.488 (or about 99.488) wt. % or about 99.49 (or about 99.49) wt. % LLDPE.

In embodiments comprising a foam wall, the foam wall is preferably a single piece of polymer foam, for example being formed by extrusion of a single extrudate. A foam wall can advantageously provide an improved level of thermal insulation for the lumen, compared with the level of thermal insulation provided by a non-foam wall. Thus, in at least one embodiment, the wall is thermally insulative of the contents (such as for example humidified gases flowing through the gas flow passage) of the elongate conduit to the potential cooling effects of the environment surrounding the medical tube (for example, insulating from the ambient air surrounding a breathing circuit, or a laparoscopic insufflation system). The environment surrounding the medical tube is for example, a hospital ward or room, an operating theater, a home bedroom, or other locations where the patient may be located.

An example method for forming a foam wall includes the addition of a chemical foaming agent to the extrudate. Chemical foaming agents are sometimes also referred to as blowing agents. A chemical foaming agent enables foaming of the extrudate material as part of or after the extrusion process.

It will also be appreciated other foaming techniques can be employed for forming a foam wall, such as by physical rather than chemical foaming methods. Physical foaming methods include gas being introduced directly into the extrudate while under pressure. As the extrudate is extruded, the pressure is reduced allowing the gas to expand. For example, one such physical foaming technique includes blowing or injecting of gas(es) into the extrudate at or near the point of extrusion. Such gas(es) may include nitrogen, carbon dioxide, pentane, or butane.

Sheath

Figure 6C:
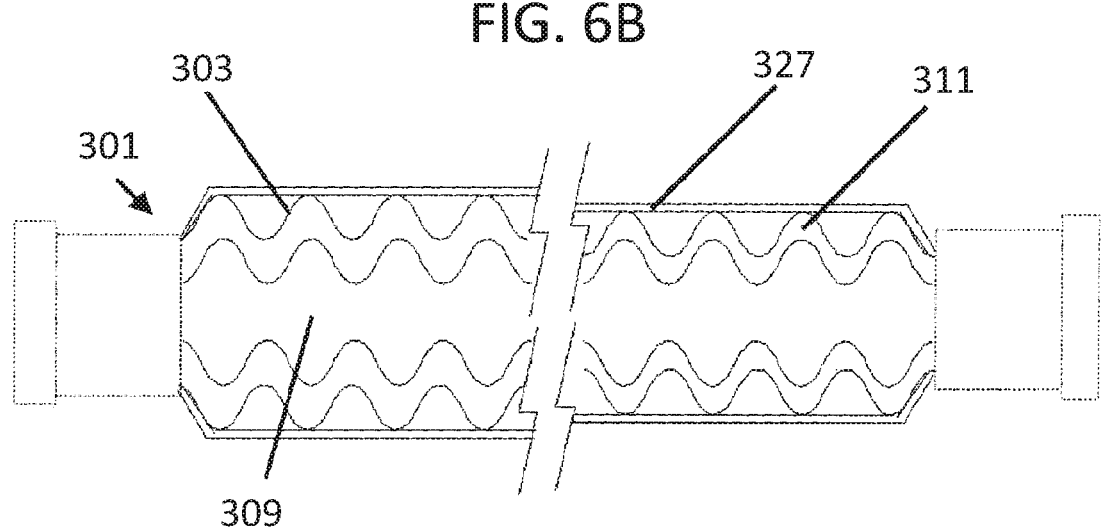

In certain embodiments, the elongate conduit 303 can further comprise a sheath 327, as shown in FIG. 6C. A sheath 327 is a member partially or fully surrounding the wall 311. The sheath 327 can be secured to the wall 311 of the conduit 303 at locations along the wall 311 or may be secured only to ends of the tube 301. The sheath may also be secured by the intermediate connector 214 of the segmented inspiratory tube 202. The sheath 327 can be used to secure conductive filaments (described below) in place and/or to prevent heat loss due to cool air currents impinging on the tube wall 311.

Although the sheath 327 can be incorporated into a conduit 303 comprising a smooth wall (not shown), a composite tube 1201 or a corrugated wall 311, it can be particularly advantageous to include such a sheath 327 with a corrugated wall or composite tube. The sheath can trap air between adjacent outer crests (or annular protrusions) of the corrugations. This may assist in further insulation of the gas passing through the lumen 309.

Where a sheath 327 is extruded about the wall 311, for example, such an extrusion could be a sequential step to initial extrusion of the wall 311, that is, an extrusion step post-formation of the wall 311. Further, where an outer sheath 327, for example, is a wrap about the wall 311, the sheath 327 may be constructed in place from a tape or ribbon spirally wound about the length of the wall 311. Still further, where an outer sheath 327 is pre-formed as a hollow tube, it may be sleeved into position about the outside of the wall 311.

In some embodiments, the sheath can be formed from a mesh, braid or fabric covering. The size of the filaments of such a sheath can be between 0.05 mm and 1.0 mm (or about 0.05 mm and 1.0 mm). Preferably, the size of the filaments is 0.25 mm (or about 0.254 mm) to 0.28 mm (or about 2.8 mm). The braided mesh may be fabricated from a variety of materials, such as plastics or metals, or natural or synthetic fibers. In one example embodiment, the sheath is preferably formed of polyethylene terephthalate monofilaments.

In one example embodiment, the sheath 27 is preferably a braided mesh surrounding one or more segments of the breathing circuit limb and is bonded to the limb only at the ends where the breathing conduit is inserted into connectors. In another example embodiment, the sheath is located outside the breathing conduit wall and is secured at and either around or underneath the end connector at the same time as the conduit wall is secured. The sheath may be secured by any suitable means as is known in the art, such as by glue, by friction fit, by overmolding, or by other conventional securing methods, In one example embodiment, the sheath may be applied to a breathing conduit as an online process where the sheath is formed at the same time as the conduit is formed, or alternatively a premade sheath may be applied to a breathing conduit in a separate process.

In use, the sheath contributes significantly to dampening the wave propagation effects of the breathing circuit limb itself (i.e. it dampens displacement of the tube). While, in some embodiments, there is no bonding between the sheath and the breathing circuit limb along the length of the conduit, it has been found that a sheath significantly improves the displacement of the tube under gas flow (in particular, high frequency gas flow). It has additionally surprisingly been found that a mesh sheath has particularly good dampening effects because, when the limb is loaded in tension (as during therapy), the axial or longitudinal stretching of the mesh causes the mesh tube to constrict radially (like a finger trap toy), which causes it to tighten around the tube and restrict or resist any wave propagation or displacement forces that may be occurring. This radial constriction is resisted by the outer surface of the tube walls (for instance, by the other surface of the first and or second elongate members of a composite tube), resulting in a strain limiting effect for the breathing circuit limb. This effect significantly improves the breathing circuit limb strength and resistance to displacement forces, while still allowing for flexible bending during positioning. In this embodiment, it is preferable to choose the material, number, weave pitch, and gauge of the braided filaments to improve the conduits stiffness. In one example embodiment of a mesh sheath, the mesh is between 10 (or about 10) to 1000 (or about 1000) picks per meter. In another example embodiment of a mesh sheath, the mesh is between 100 (or about 100) to 500 (or about 500) picks per meter. In another example embodiment of a mesh sheath, the mesh is between 200 (or about 200) to 400 (or about 400) picks per meter. Dampening displacement of the tube can generally refer to restricting or resisting any wave propagation or displacement forces that may be experienced by the tube when it is under tension, such as during therapy. This can result in various dampening effects during therapy, such as a reduced magnitude of displacement, a reduction in the displacement frequency, a reduction in the curvature of bends of the tube, and/or a general reduction in noticeable movement of the tube.

The mesh sheath may comprise a single strand or filament, or more than one adjacent strand or filament. For example, apart from a single strand, the mesh sheath may also be made up of between 2 and 32 adjacent filaments. There may be 1 or 2 or 4 or 8 or 16 or 32 or 64 or more adjacent strands in the sheath. There may be any suitable number of braids (containing one or more filaments as discussed above) to achieve the desired picks per meter. For example, there may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more braids. In one example embodiment, a suitable mesh may have in the range of 250-350 picks per meter, made up of 36 braids containing 2 adjacent filaments per braid.

Alternate Dampening Features

It should be appreciated by one of skill in the art that there are other suitable means for resisting displacement forces while still allowing flexibility in a bending motion, such as by attaching at least one component with a different harmonic frequency response from the tube itself.

In one example embodiment, a dampening feature is spline, or at least one spline. The spline may be internal (in the lumen or in the sidewall) or external to the tube, formed at the same time as the tube or at a separate time as the tube, formed integrally with the tube or not, extending along substantially the length of a segment of the tube or extending only a partial length of the segment of the tube, co-axial with the tube, or not.

In another example embodiment, a dampening feature is at least one stiffening rod (which formed of a material such that it is still flexible under bending forces). The stiffening rod may be internal (in the lumen or in the sidewall) or external to the tube, formed at the same time as the tube or at a separate time as the tube, formed integrally with the tube or not, extending along substantially the length of a segment of the tube or extending only a partial length of the segment of the tube, co-axial with the tube or not.

In one example embodiment, a dampening feature is at least one rib. The rib may be internal (in the lumen or in the sidewall) or external to the tube, formed at the same time as the tube or at a separate time as the tube, formed integrally with the tube or not, extending along substantially the length of a segment of the tube or extending only a partial length of the segment of the tube, extending axially along the tube or not, extending radially about the tube or not, extending perpendicular to the axis of the tube or not.

In one example embodiment, a dampening feature is at least one film. The film may be internal (in the lumen or in the sidewall) or external to the tube, formed at the same time as the tube or at a separate time as the tube, formed integrally with the tube or not, overlaid over the tube or within the tube, extending along substantially the length of a segment of the tube or extending only a partial length of the segment of the tube, co-axial with the tube or not.

In one example embodiment, the dampening feature is a tape, or strip, or string. The tape or strip or string may be internal (in the lumen or in the sidewall) or external to the tube, formed at the same time as the tube or at a separate time as the tube, formed integrally with the tube or not, overlaid over the tube or within the tube, extending along substantially the length of a segment of the tube or extending only a partial length of the segment of the tube, co-axial with the tube or not. The tape or strip or string may include adhesive on one or more sides, extending partially or wholly along the length of the tape or strip or string, or it may not include any adhesive and will be retained on or within the tube in any other suitable manner, such as those described elsewhere in this specification. The tape or strip or string may be helically wound about the tube. Preferably, where the tube is made up of helically wound components, the helically wound tape or strip or string is at a different pitch than the helically wound components of the tube (either looser or tighter pitches). In an alternative embodiment, the tape or strip or string is not helically wound. In a further example embodiment, the tape or strip or string may extend longitudinally along the tube. In another further example embodiment, the tape or strip or string includes at least one segment that is helically wound and at least one segment that is not helically wound.

The end or intermediate connector(s) may also structural features to receive the dampening features described above, such as a recess or groove, a lip, or a slot. For instance, in one example embodiment, at least one connector (such as an end connector or intermediate connector) comprises a recess or groove for receiving a reinforcing spine as described above. It should be appreciated that such dampening features may be retained by the connector(s) by conventional attachment means in the art, such as adhesives, friction fit, or overmolding. It should further be appreciate by one of skill in the art that such dampening features may be made of any suitable material, such as plastics, metal, natural or synthetic fibers, silicone, or other suitable materials, including those described elsewhere in this specification.

Flexible Breathing Tubes

FIGS. 7A-7B and 8A-8E illustrate embodiments of various flexible breathing tubes. Flexible tubes can be used to improve positionality and usability of tubes when providing respiratory therapy to patients, especially neonatal patients. Use of low weight flexible tube within a respiratory humidification system can cause the tubes to experience vibrations and displacement when certain respiratory waveforms are transmitted through the breathing tube, for example when performing high frequency oscillatory ventilation. In some instances, the vibration can cause significant displacement of the breathing tubes that may be displeasing or concerning to patient caregivers, such as prescribing doctors, nurses, therapists, or friends and family members. Moreover, a more rigid tube may be more difficult to position appropriately, and may result in application of a force load on the patient interface that can be uncomfortable to the patient or may even cause injury. The embodiments described with respect to FIGS. 7A-7B and 8A-8E provide various solutions for dampening and controlling oscillations and displacement of the breathing tubes during operation.

With reference to FIGS. 7A-7B and 8A-8D, the breathing tubes have a first segment 402a and a second segment 402b with an intermediate connector 414 between the first segment 402a and the second segment 402b. The first segment 402a can include humidifier interface connector 404 that has a suitable fitting for coupling with humidification chamber at one end and the intermediate connector 414 at the opposite end. The second segment 402b can have a patient interface connector 406 that has a suitable fitting for coupling with a patient interface a one end and the intermediate connector 414 at the opposite end. The segments of the tube 402a, 402b can be coupled to one another by the intermediate connector to form a single conduit for gas delivery. The first segment 402a, the second segment 402b, and the intermediate connector 414 can be configured in accordance with the various embodiments disclosed herein. For example, the segments 402a, 402b, can be implemented in accordance with the segments 202a and 202b, respectively and the intermediate connector 414 can be implemented in accordance with intermediate connector 214.

The second segment 402b can be shorter than the first segment 402a, and, in certain implementations, the second segment 402b can be about half as long as the first segment 402a. The first segment 402a, for example, can have a length that is at least about 0.5 m and/or less than or equal to about 2 m, at least about 0.7 m and/or less than or equal to about 1.8 m, at least about 0.9 m and/or less than or equal to about 1.5 m, or at least about 1 m and/or less than or equal to about 1.2 m. The second segment 402b, for example, can have a length that is at least about 0.2 m and/or less than or equal to about 1.5 m, at least about 0.3 m and/or less than or equal to about 1 m, at least about 0.4 m and/or less than or equal to about 0.8 m, or at least about 0.5 m and/or less than or equal to about 0.7 m.

Figure 7A:
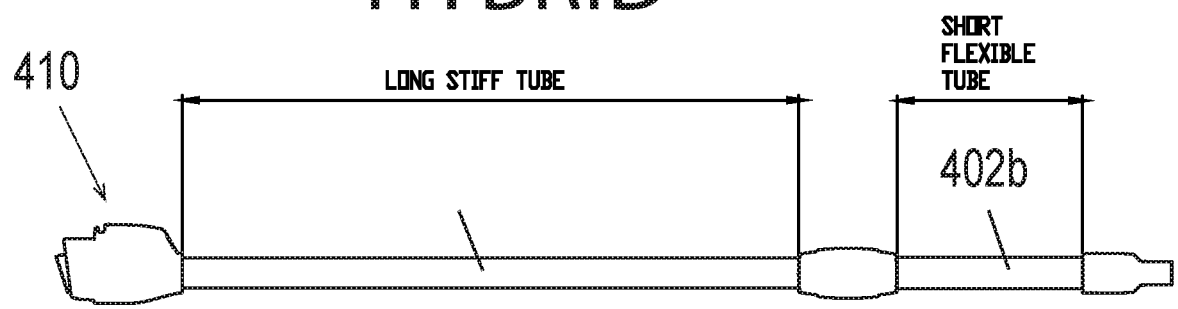
FIGS. 7A-7B show an example of a breathing tube having a first section and a second section with different flexibilities.
Figure 7B:
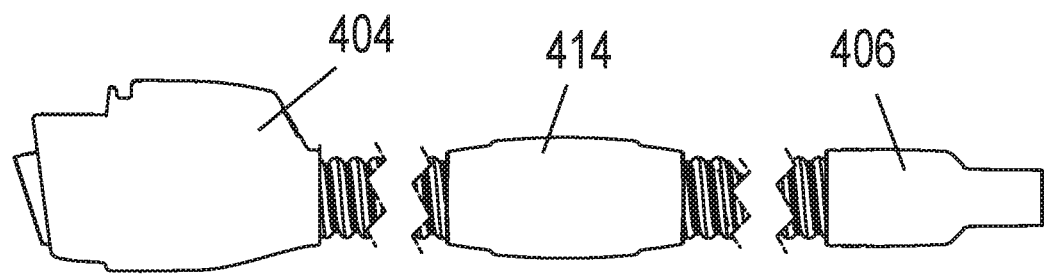

With reference to FIGS. 7A and 7B, an embodiment of the breathing tube 410 is illustrated. The first segment 402a and the second segment 402b of the breathing tube 410 have different flexibilities. The first segment 402a is stiffer and has a higher stiffness or rigidity than the second segment 402b. The second segment 402b closer to the patient interface has greater flexibility than the first segment 402a. In some embodiments, the first segment and/or the second segment can have a variable stiffness, such as described with respect to FIGS. 6A-6C. For example, the first segment 402a can have a constant stiffness and the second segment 402b can have a variable stiffness along the length of the segment so that the portion of the second segment 402b closest to the patient interface has the highest flexibility. By including a stiffer segment 402a the oscillations and displacement in the larger segment of the tube can be reduced and dampened. The relative flexibilities of the first segment 402a and the second segment 402b can be controlled by altering the structure of the tube. In some embodiments, the segments 402a, 402b of the tube can be a composite tube and the flexibilities can be altered as discussed herein with respect to FIGS. 5A-5E. For example, the more flexible second segment 402b can have, relative to the stiffer first segment 402a, at least one of a thinner sidewall, smaller inner diameter, tighter pitch, and/or a smaller bead width. In some embodiments, the first elongate member (e.g., 1203) of the second segment 402b is narrower and taller than the first elongate member of the first segment 402a.

Additionally, the first segment 402a and the second segment 402b may be made up of different materials. This may result in the first segment 402a and the second segment 402b having a different stiffness/flexibility. Alternatively, the different materials may be selected such that the first segment 402a and the second segment 402b have similar stiffness/flexibility. In one example embodiment, the different materials are a same material having different durometers and/or viscosities. In another example embodiment, the different materials are a different family or class or type of material.

In another example embodiment, one or more segments may undergo post-processing to make the segment more or less flexible. For instance, the one or more segments may undergo crosslinking post extrusion. In a further example embodiment, the crosslinking agent may be externally cured (i.e., cured on the external surface of the tube), but left uncured on the inner surface of the tube. Alternatively, the opposite may be done, where the inside surface of the tube is cured, but not the external surface. In a further example embodiment, one or more segments of a multi-segmented tube may include such post-processing, while other segments of the multi-segmented tube do not.

With reference to FIGS. 8A-8E illustrate embodiments of a breathing tube 420 with a sheath 408 overlaying one or more segments of the tube 420. The first segment 402a and the second segment 402b can have the same flexibility. The sheath 408 can be similar the sheath 327 described with respect to FIG. 6C. The sheath 408 can partially or fully surround the outer wall of segments and/or connectors of the tube 420. The sheath 408 may be applied about wall as an extruded outer layer, as a wrapping about the wall, or as a sleeve that is slid or pulled into position about the wall. The sheath 408 may be of any necessary thickness, although thickness and the material used should be balanced with the need to maintain flexibility of the tube. The sheath can be formed from a mesh, braid or fabric covering. The sheath 408 can be a secured at one or more locations along the tube or may be secured only to ends of segments of the tube, such as the intermediate connector, the patient interface, and/or the humidifier interface.

The mesh or braided sheath may include a substantial number of apertures between the threads which are open to the ambient environment. Where those apertures are wide, it should be appreciated that the mesh or braided sheath does not act as a significant insulating layer. However, applicants have surprisingly found that a mesh or braided sheath acts to dampen or absorb displacement or movement of the tube during therapy, bringing amount of displacement or movement down to levels that are commonplace and acceptable to caregivers. Moreover, applicants have found that such mesh or braided sheaths do not inhibit or restrict the flexibility of the tube.

Figure 8A:
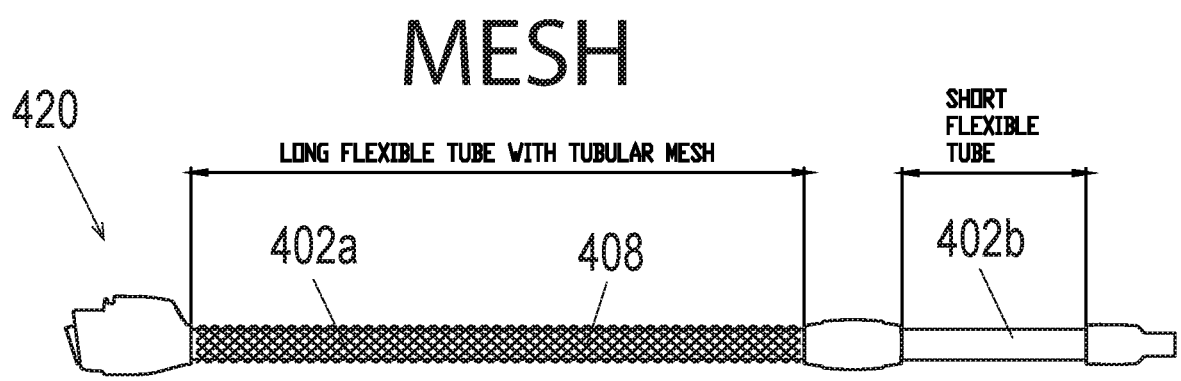
FIGS. 8A-8E show examples of breathing tubes having a first section and a second section with a mesh disposed on one or more sections of the breathing tube.
Figure 8B:
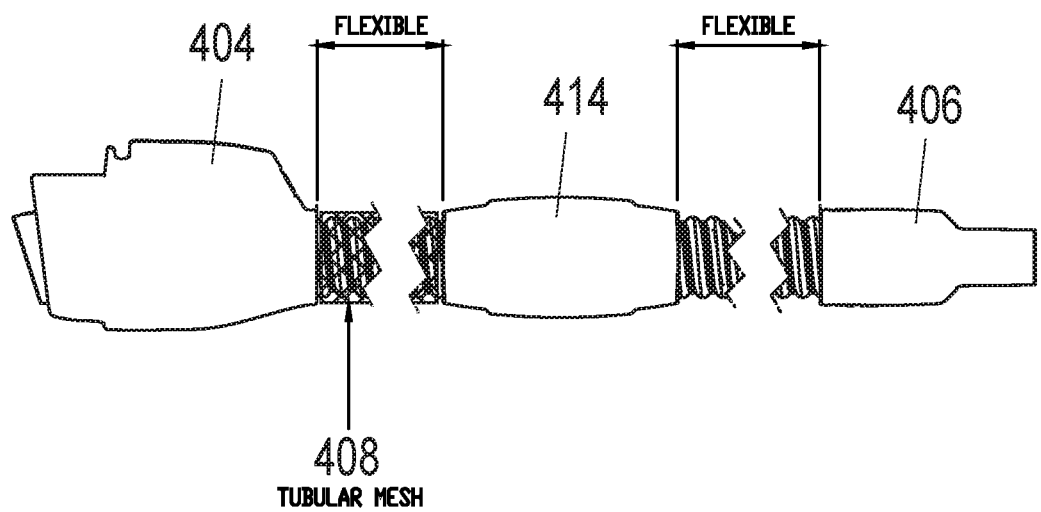
Figure 8C:
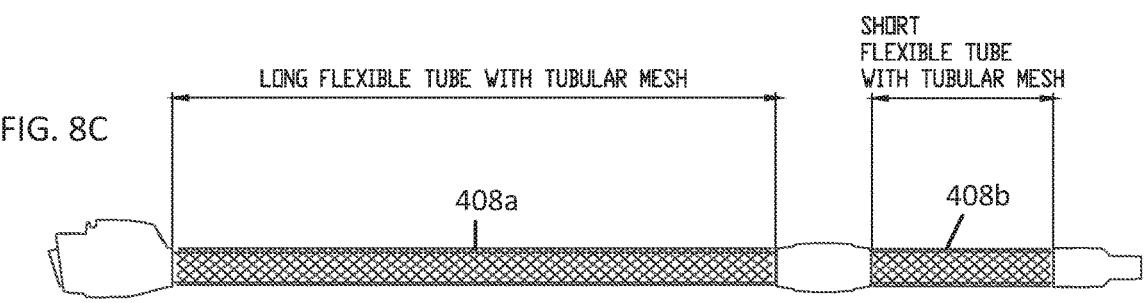
Figure 8D:
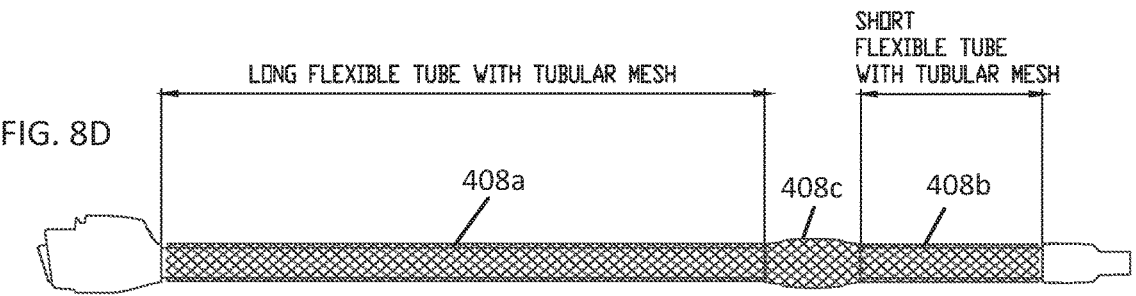
Figure 8E:
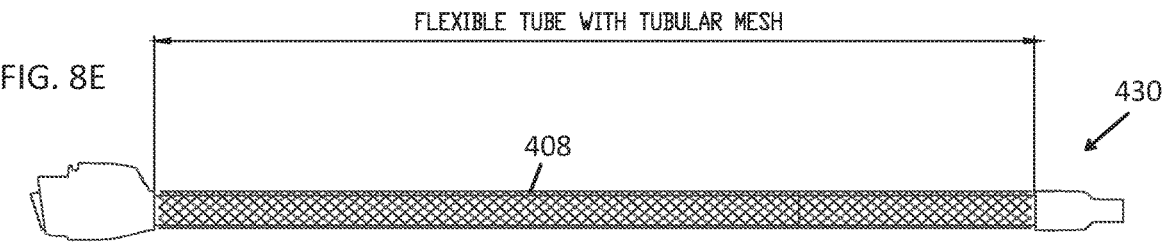

In FIG. 8A, the sheath is overlayed on the first segment 402a of the tube 420. In FIG. 8C, a first sheath 408a is overlayed on the first segment 402a of the tube and a second sheath 408b is overlayed on the second segment 402b. In another example embodiment similar to FIG. 8C, the sheath may be continuous along the whole length of the tube, passing underneath the intermediate connector. In FIG. 8D, a first sheath segment 408a is overlayed on the first segment 402a of the tube, a second sheath segment 408b is overlayed on the second segment 402b, and a third sheath segment 408c is overlayed on the intermediate connector 414. The sheath segments 408a-c can be a single sheath that extends from the humidifier interface connector 404 to the patient interface connector 406. In some embodiments, the sheaths can be divided into to two or more sheaths. FIG. 8E illustrates an embodiment of a tube 430 that includes only a single flexible tube segment between the humidifier interface connector 404 to the patient interface connector 406. The tube 430 has a sheath 408 that extends the entire length of the tube. In one example embodiment, the sheath is a thin-walled sheath.

It should be appreciated from FIGS. 7 and 8 that all combinations of flexibility, multiple or single segments, and sheaths may be used based on this disclosure. Similarly, a composite (or bubble) tube may be more or less flexible because of any of the modifications described with reference to FIG. 5. For instance, a segmented tube with intermediate connector may be provided with the same flexibility between the segments. This tube may be more flexible than other tubes because the first member having a hollow body has a thinner sidewall near the lumen of the tube than it has at the sidewall exposed to the atmosphere, or it may be more flexible than other tubes based on the other parameters described with reference to FIG. 5. This tube may have a sheath over one or all segments, and the sheath may pass over or under the intermediate connector. Alternatively, the tube may be a single segment tube with a constant flexibility along its length, as shown in FIG. 8E. This tube includes a sheath over the whole length. In another embodiment, the tube in 8E includes a sheath over only a portion of the length of the tube. In another embodiment, the single tube in FIG. 8E may have a variable flexibility along its length, as shown in FIG. 6. Alternatively, a tube may be provided with different segments having different or the same flexibility between the segments. For instance, the patient end segment may have more, less, or equal flexibility to the humidifier end segment. Similarly, if there are more than two segments, the segments may have more, less, or equal flexibility to other segments of the tube.

Examples of respiratory humidification systems and associated components and methods have been described with reference to the figures. The figures show various systems and modules and connections between them. The various modules and systems can be combined in various configurations and connections between the various modules and systems can represent physical or logical links. The representations in the figures have been presented to clearly illustrate the principles and details regarding divisions of modules or systems have been provided for ease of description rather than attempting to delineate separate physical embodiments. The examples and figures are intended to illustrate and not to limit the scope of the inventions described herein. For example, the principles herein may be applied to a respiratory humidifier as well as other types of humidification systems, including surgical humidifiers. The principles herein may be applied in respiratory applications as well as in other scenarios where a temperature of gases is to be controlled along multiple segments subject to varying ambient temperatures.

As used herein, the term "processor" refers broadly to any suitable device, logical block, module, circuit, or combination of elements for executing instructions. For example, the controller 122 can include any conventional general purpose single- or multi-chip microprocessor such as a Pentium® processor, a MIPS® processor, a Power PC® processor, AMD® processor, ARM® processor, or an ALPHA® processor. In addition, the controller 122 can include any conventional special purpose microprocessor such as a digital signal processor or a microcontroller. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein, or can be a pure software in the main processor. For example, logic module 504 can be a software-implemented function block which does not utilize any additional and/or specialized hardware elements. Controller 122 can be implemented as a combination of computing devices, e.g., a combination of a DSP and a microprocessor, a combination of a microcontroller and a microprocessor, a plurality of microprocessors, one or more microprocessors in conjunction with a DSP core, or any other such configuration.

Data storage can refer to electronic circuitry that allows data to be stored and retrieved by a processor. Data storage can refer to external devices or systems, for example, disk drives or solid state drives. Data storage can also refer to fast semiconductor storage (chips), for example, Random Access Memory (RAM) or various forms of Read Only Memory (ROM), which are directly connected to the communication bus or the controller 122. Other types of data storage include bubble memory and core memory. Data storage can be physical hardware configured to store data in a non-transitory medium.

Although certain embodiments and examples are disclosed herein, inventive subject matter extends beyond the specifically disclosed embodiments to other alternative embodiments and/or uses, and to modifications and equivalents thereof. Thus, the scope of the claims or embodiments appended hereto is not limited by any of the particular embodiments described herein. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z each to be present. As used herein, the words "about" or "approximately" can mean a value is within ±10%, within ±5%, or within ±1% of the stated value.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A breathing tube comprising:
    a humidifier end segment of the breathing tube, wherein the humidifier end segment is a composite tube having a first elongate member comprising a hollow body spirally wound to form at least part of the breathing tube, and a second elongate member spirally wound and joined between adjacent turns of the first elongate member, the second elongate member forming at least a portion of a lumen of the breathing tube;
    a patient interface end segment of the breathing tube;
    an intermediate connector connecting the humidifier end segment to the patient interface end segment; and
    a sheath overlaying the humidifier end segment, wherein the sheath is configured to maintain flexibility and dampen displacement during gas flow, wherein no sheath overlays the patient interface end segment.

2. The breathing tube of claim 1, wherein the intermediate connector secures at least one end of the sheath.

3. The breathing tube of claim 1, wherein the sheath extends at least a partial length of the humidifier end segment.

4. The breathing tube of claim 1, wherein the sheath extends substantially along a whole length of the humidifier end segment.

5. The breathing tube of claim 1, wherein the sheath is configured to dampen displacement of the breathing tube by restricting or resisting wave propagation or oscillation or displacement during therapy.

6. The breathing tube of claim 1, wherein the patient interface end segment is configured to connect to a patient interface.

7. The breathing tube of claim 1, wherein the sheath is a mesh.

8. The breathing tube of claim 1, wherein the intermediate connector is configured to releasably couple the humidifier end segment and the patient interface end segment.

9. A breathing tube comprising:
    a humidifier end segment of the breathing tube having a first flexibility;
    a patient interface end segment of the breathing tube having a second flexibility, wherein the second flexibility is the same as the first flexibility;
    an intermediate connector connecting the humidifier end segment to the patient interface end segment; and
    a sheath overlaying the humidifier end segment, wherein the sheath is configured to maintain flexibility and dampen displacement during gas flow, wherein no sheath overlays the patient interface end segment.

10. The breathing tube of claim 9, wherein the intermediate connector secures at least one end of the sheath.

11. The breathing tube of claim 9, wherein the sheath extending at least a partial length of the humidifier end segment.

12. The breathing tube of claim 9, wherein the sheath extending substantially along a whole length of the humidifier end segment.

13. The breathing tube of claim 9, wherein the humidifier end segment is a composite tube having a first elongate member comprising a hollow body spirally wound to form at least in part of the breathing tube, and a second elongate member spirally wound and joined between adjacent turns of the first elongate member, the second elongate member forming at least a portion of a lumen of the breathing tube.

14. The breathing tube of claim 9, wherein the sheath is configured to dampen displacement of the breathing tube by restricting or resisting wave propagation or oscillation or displacement during therapy.

15. A breathing tube comprising:
    a humidifier end segment of the breathing tube having a first flexibility;
    a patient interface end segment of the breathing tube having a second flexibility, wherein the second flexibility is the same as the first flexibility;
    an intermediate connector connecting the humidifier end segment to the patient interface end segment; and
    a single sheath, wherein the single sheath overlays the humidifier end segment, wherein the single sheath is configured to maintain flexibility and dampen displacement during gas flow, wherein the single sheath does not overlay the patient interface end segment.

16. The breathing tube of claim 15, wherein the intermediate connector secures at least one end of the single sheath.

17. The breathing tube of claim 15, wherein the single sheath extending at least a partial length of the humidifier end segment.

18. The breathing tube of claim 15, wherein the single sheath extending substantially along a whole length of the humidifier end segment.

19. The breathing tube of claim 15, wherein the humidifier end segment is a composite tube having a first elongate member comprising a hollow body spirally wound to form at least in part of the breathing tube, and a second elongate member spirally wound and joined between adjacent turns of the first elongate member, the second elongate member forming at least a portion of a lumen of the breathing tube.

20. The breathing tube of claim 15, wherein the single sheath is configured to dampen displacement of the breathing tube by restricting or resisting wave propagation or oscillation or displacement during therapy.

* * * * *